US012778681B2

(12) United States Patent
Uchitel et al.

(10) Patent No.: US 12,778,681 B2
(45) Date of Patent: Nov. 3, 2026

(54) PLASMA CONTROL

(71) Applicant: CAPS Medical Ltd., Netanya (IL)

(72) Inventors: Ilan Oleg Uchitel, Kfar-Saba (IL); Boris Kogan, Kiriat-Motzkin (IL)

(73) Assignee: CAPS Medical Ltd., Netanya (IL)

( * ) Notice: Subject to any disclaimer, the term of this patent is extended or adjusted under 35 U.S.C. 154(b) by 194 days.

(21) Appl. No.: 18/566,759

(22) PCT Filed: Jun. 3, 2022

(86) PCT No.: PCT/IL2022/050595
§ 371 (c)(1),
(2) Date: Dec. 4, 2023

(87) PCT Pub. No.: WO2022/254447
PCT Pub. Date: Dec. 8, 2022

(65) Prior Publication Data

US 2024/0206975 A1 Jun. 27, 2024

Related U.S. Application Data

(60) Provisional application No. 63/196,251, filed on Jun. 3, 2021.

(51) Int. Cl.
*A61B 34/10* (2016.01)
*A61B 18/00* (2006.01)
(Continued)

(52) U.S. Cl.
CPC .............. *A61B 34/10* (2016.02); *A61B 18/00* (2013.01); *A61B 34/20* (2016.02); *A61B 34/32* (2016.02);
(Continued)

(58) Field of Classification Search
CPC ......... A61B 34/10; A61B 18/00; A61B 34/20; A61B 34/32; A61B 90/06;
(Continued)

(56) References Cited

U.S. PATENT DOCUMENTS 3,903,891 A 9/1975 Brayshaw
4,092,485 A 5/1978 Wanser
(Continued)

FOREIGN PATENT DOCUMENTS

CN 103765552 4/2014
CN 203763232 8/2014
(Continued)

OTHER PUBLICATIONS

Notice of Allowance Dated Apr. 23, 2024 from the US Patent and Trademark Office Re. U.S. Appl. No. 17/319,157. (8 pages).
(Continued)

*Primary Examiner* — Brian T Gedeon

(57) ABSTRACT

Systems and methods for controlling plasma dosage; particularly, in some embodiments, using small diameter intra-body plasma delivery probes. Control of administration of a selected dosage of plasma to be applied to tissue may include selection of a pattern of motion of the probe as it moves to deliver plasma: not only to where, but also for how long the probe remains and/or at what speed the probe moves. In some embodiments, feedback from measurements is used to help ensure the targeted dosage of plasma is delivered; for example measurements of power which generates plasma, and/or spectral characteristics of generated plasma. In some embodiments, a joint relationship between probe position and plasma generation exists, such that maximum power is obtained at a certain distance from the target which allows the plasma plume to fully develop, rate of plasma delivery, accordingly, may itself be adjusted by motions of the plasma delivering probe.

28 Claims, 9 Drawing Sheets

(51) Int. Cl.

| | |
|---|---|
| ***A61B 34/20*** | (2016.01) |
| ***A61B 34/32*** | (2016.01) |
| ***A61B 90/00*** | (2016.01) |
| ***A61N 1/02*** | (2006.01) |
| ***A61N 1/08*** | (2006.01) |
| ***A61N 1/44*** | (2006.01) |

(52) U.S. Cl.
CPC .............. *A61B 90/06* (2016.02); *A61N 1/025* (2013.01); *A61N 1/08* (2013.01); *A61N 1/44* (2013.01); *A61B 2018/00779* (2013.01); *A61B 2018/00863* (2013.01); *A61B 2034/104* (2016.02); *A61B 2034/2046* (2016.02)

(58) Field of Classification Search
CPC ........... A61B 2018/00779; A61B 2018/00863; A61B 2034/104; A61B 2034/2046; A61B 2034/2061; A61B 2090/378; A61B 34/30; A61B 18/042; A61B 2018/00285; A61B 2018/00345; A61B 2018/00648; A61B 2018/00744; A61B 2018/00791; A61B 2018/00875; A61B 2034/2059; A61B 2034/301; A61B 2090/376; A61B 2090/3966; A61N 1/025; A61N 1/08; A61N 1/44
See application file for complete search history.

(56) References Cited

U.S. PATENT DOCUMENTS

| | | | |
|---|---|---|---|
| 5,088,997 | A | 2/1992 | Delahuerga et al. |
| 5,130,003 | A | 7/1992 | Conrad |
| 5,977,715 | A | 11/1999 | Li et al. |
| 6,099,523 | A | 8/2000 | Kim et al. |
| 6,213,999 | B1 | 4/2001 | Platt et al. |
| 6,565,558 | B1 | 5/2003 | Lindenmeier et al. |
| 6,958,063 | B1 | 10/2005 | Soll et al. |
| 7,316,682 | B2 | 1/2008 | Konesky |
| 7,572,998 | B2 | 8/2009 | Mohamed et al. |
| 7,608,839 | B2 | 10/2009 | Coulombe et al. |
| 7,785,322 | B2 | 8/2010 | Penny et al. |
| 8,077,094 | B2 | 12/2011 | Anderson et al. |
| 8,187,265 | B2 | 5/2012 | Choi et al. |
| 8,232,729 | B2 | 7/2012 | Kitano et al. |
| 8,267,884 | B1 | 9/2012 | Hicks |
| 8,725,248 | B2 | 5/2014 | Gutsol et al. |
| 8,834,462 | B2 | 9/2014 | Johnson et al. |
| 11,006,994 | B2 | 5/2021 | Krasik et al. |
| 2001/0000206 | A1 | 4/2001 | Li et al. |
| 2004/0030334 | A1 | 2/2004 | Quick et al. |
| 2005/0118350 | A1 | 6/2005 | Koulik et al. |
| 2006/0189976 | A1 | 8/2006 | Karni |
| 2007/0038208 | A1 | 2/2007 | Kefer |
| 2010/0100094 | A1 | 4/2010 | Truckai |
| 2011/0112528 | A1 | 5/2011 | Stieber et al. |
| 2011/0140607 | A1 | 6/2011 | Moore et al. |
| 2012/0029506 | A1 | 2/2012 | Johnson |
| 2012/0107896 | A1 | 5/2012 | Wandke et al. |
| 2012/0153332 | A1 | 6/2012 | Tu et al. |
| 2012/0167089 | A1 | 6/2012 | Vermande et al. |
| 2012/0245580 | A1 | 9/2012 | Germain et al. |
| 2012/0283732 | A1 | 11/2012 | Lam |
| 2012/0288405 | A1 | 11/2012 | Snowball |
| 2012/0289954 | A1 | 11/2012 | Lam |
| 2013/0053762 | A1 | 2/2013 | Rontal et al. |
| 2013/0199540 | A1 | 8/2013 | Buske |
| 2014/0005646 | A1 | 1/2014 | Temelkuran et al. |
| 2014/0061025 | A1 | 3/2014 | Bauer et al. |
| 2014/0074090 | A1 | 3/2014 | Lam et al. |
| 2015/0038790 | A1 | 2/2015 | Rontal et al. |
| 2015/0313670 | A1 | 11/2015 | Shroff et al. |
| 2015/0342663 | A1 | 12/2015 | Canady et al. |
| 2017/0014998 | A1 | 1/2017 | Langenfeld et al. |
| 2017/0354453 | A1 | 12/2017 | Krasik et al. |
| 2018/0064496 | A1 | 3/2018 | Hladio et al. |
| 2020/0038530 | A1 | 2/2020 | Yildirim et al. |
| 2020/0069355 | A1 | 3/2020 | Kcidar |
| 2020/0275979 | A1 | 9/2020 | Canady et al. |
| 2021/0338304 | A1 | 11/2021 | Krasik et al. |
| 2023/0093858 | A1 * | 3/2023 | Roman ................ A61B 18/042 606/41 |

FOREIGN PATENT DOCUMENTS

| | | |
|---|---|---|
| CN | 107106225 | 8/2017 |
| EP | 0694290 | 1/1996 |
| EP | 1658817 | 5/2006 |
| EP | 1832243 | 9/2007 |
| JP | 2014-506502 | 3/2014 |
| JP | 2021-506365 | 2/2021 |
| WO | WO 2012/153332 | 11/2012 |
| WO | WO 2012/167089 | 12/2012 |
| WO | WO 2014/061025 | 4/2014 |
| WO | WO 2016/079742 | 5/2016 |
| WO | WO 2021/092324 | 5/2021 |
| WO | WO 2021/186449 | 9/2021 |
| WO | WO 2022/254447 | 12/2022 |
| WO | WO 2022/254448 | 12/2022 |

OTHER PUBLICATIONS

Notice of Reason(s) for Rejection Dated Nov. 25, 2025 From the Japan Patent Office Re. Application No. 2023-574471 and Its Translation Into English. (7 Pages).
Summons to Attend Oral Proceedings Pursuant to Rule 115(1) EPC Dated Nov. 25, 2025 From the European Patent Office Re. Application No. 15813925.3 (18 Pages).
Communication of a Letter of Opponent Dated May 3, 2024 From the European Patent Office Re. Application No. 15813925.3. (24 Pages).
Brief Communicaation Dated Apr. 13, 2023 From the European Patent Office Re. Application No. 15813925.3. (11 Pages).
Communication of a Decision Revoking EP Patent Article 101(2) EPC Dated Jul. 10, 2023 From the European Patent Office Re. Application No. 15813925.3. (51 Pages).
Communication of a Notice of Opposition Dated May 27, 2022 From the European Patent Office Re. Application No. 15813925.3. (24 Pages).
Communication Pursuant to Article 94(3) EPC Dated Aug. 28, 2020 From the European Patent Office Re. Application No. 15813925.3. (6 Pages).
International Preliminary Report on Patentability Dated Sep. 6, 2023 From the International Preliminary Examining Authority Re. Application No. PCT/IL2022/050596 (29 Pages).
International Preliminary Report on Patentability Dated Sep. 13, 2023 From the International Preliminary Examining Authority Re. Application No. PCT/IL2022/050595 (30 Pages).
International Preliminary Report on Patentability Dated May 23, 2017 From the International Bureau of WIPO Re. Application No. PCT/IL2015/051116. (8 Pages).
International Search Report and the Written Opinion Dated Oct. 4, 2022 From the International Searching Authority Re. Application No. PCT/IL2022/050595. (17 Pages).
International Search Report and the Written Opinion Dated Jan. 20, 2023 From the International Searching Authority Re. Application No. PCT/IL2022/050596. (17 Pages).
International Search Report and the Written Opinion Dated Feb. 22, 2016 From the International Searching Authority Re. Application No. PCT/IL2015/051116. (13 Pages).
Interview Summary Dated Dec. 6, 2023 from the US Patent and Trademark Office Re. U.S. Appl. No. 17/319,157. (7 pages).
Invitation to Pay Additional Fees Dated Apr. 21, 2023 From the International Searching Authority Re. Application No. PCT/IL2022/050596. (3 Pages).
Invitation to Pay Additional Fees, Communication Relating to the Results of the Partial International Search and the Provisional

(56) References Cited

OTHER PUBLICATIONS

Opinion Dated Nov. 2, 2022 From the International Searching Authority Re. Application No. PCT/IL2022/050596. (11 Pages).
Notice of Allowance Dated Jan. 21, 2021 from the US Patent and Trademark Office Re. U.S. Appl. No. 15/527,499. (5 pages).
Notification of Office Action and Search Report Dated May 22, 2019 From the China National Intellectual Property Administration Re. Application No. 201580069489.0 and Its Translation Into English. (18 Pages).
Notification of Office Action and Search Report Dated Dec. 25, 2020 From the State Intellectual Property Office of the People's Republic of China Re. Application No. 201580069489.0 and Its Translation of Office Action Into English. (11 Pages).
Notification of Office Action Dated Apr. 3, 2020 From the China National Intellectual Property Administration Re. Application No. 201580069489.0. (6 Pages).
Office Action Dated Sep. 8, 2020 From the Israel Patent Office Re. Application No. 252332 and Its Translation Into English. (5 Pages).
Official Action Dated May 2, 2019 From the US Patent and Trademark Office Re. U.S. Appl. No. 15/527,499. (17 Pages).
Official Action Dated Oct. 18, 2023 from the US Patent and Trademark Office Re. U.S. Appl. No. 17/319,157. (34 pages).
Official Action Dated Oct. 21, 2019 From the US Patent and Trademark Office Re. U.S. Appl. No. 15/527,499. (21 pages).
Official Action Dated Sep. 8, 2020 from the US Patent and Trademark Office Re. U.S. Appl. No. 15/527,499. (13 pages).
Summons to Attend Oral Proceedings Pursuant to Rule 115(1) EPC Dated Dec. 20, 2022 From the European Patent Office Re. Application No. 15813925.3. (34 Pages).
Translation Dated May 18, 2020 of Notification of Office Action Dated Apr. 3, 2020 From the China National Intellectual Property Administration Re. Application No. 201580069489.0. (7 Pages).
Fridman et al. "Floating Electrode Dielectric Barrier Discharge Plasma in Air Promoting Apoptotic Behavior in Melanoma Skin Cancer Cell Lines", Plasma Chemistry and Plasma Processing 27(2):163-176, Apr. 2007.
Graves "Low Temperature Plasma Biomedicine: A Tutorial Review", AIP Physics of Plasmas, 21: 080901, Aug. 7, 2014.
Hirst et al. "Low Temperature Plasma: A Novel Focal Therapy For Localized Prostate Cancer?", BioMed Research International, 2014, Art. 878319, 15 Pages, Mar. 13, 2014.
Keidar et al. "Cold Plasma Selectivity and the Possibility of a Paradigm Shift in Cancer Therapy", British Journal of Cancer, 105: 1295-1301, Oct. 25, 2011.
Robert et al. "Perspectives of Endoscopic Plasma Applications", Clinical PlasmaMedicine, 1(2): 8-16, Dec. 2013.
Schlegel et al. "Plasma In Cancer Treatment", Clinical Plasma Medicine, 1(2): 2-7, 2013.
Notification of Office Action Dated Mar. 27, 2026 From the National Intellectual Property Administration of the People's Republic of China Re. Application No. 202280053387.X and Its Translation Into English. (8 Pages).
Official Action Dated May 27, 2026 from the US Patent and Trademark Office Re. U.S. Appl. No. 18/566,718. (45 pages).

* cited by examiner

FIG. 4A
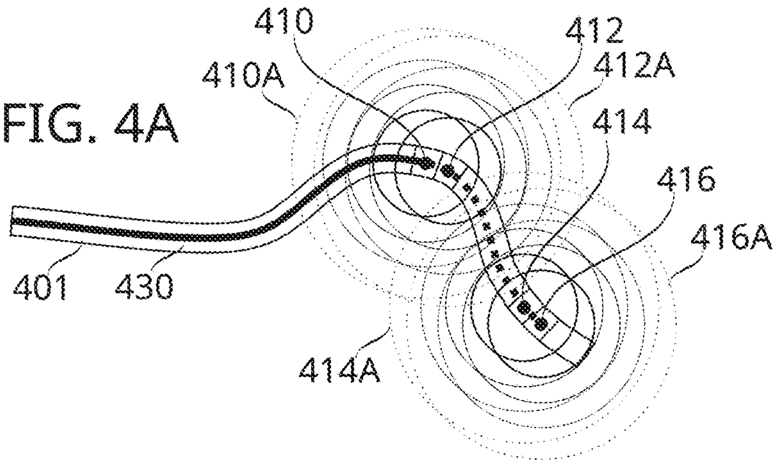
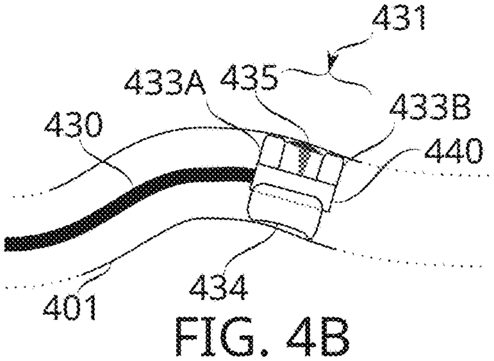
FIG. 4B
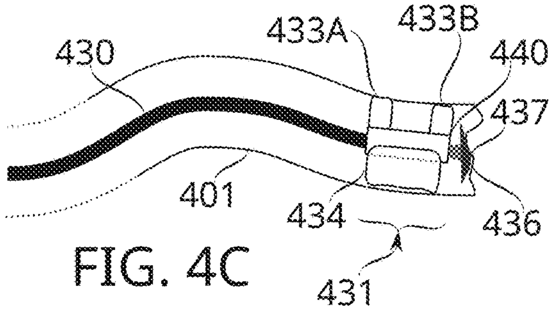
FIG. 4C
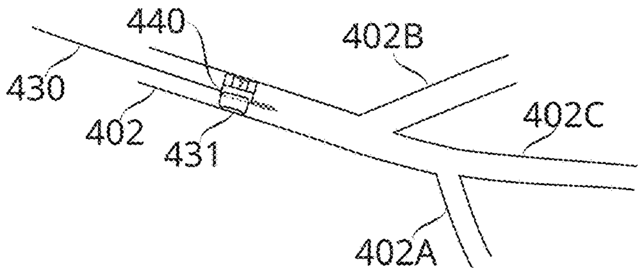
FIG. 4D
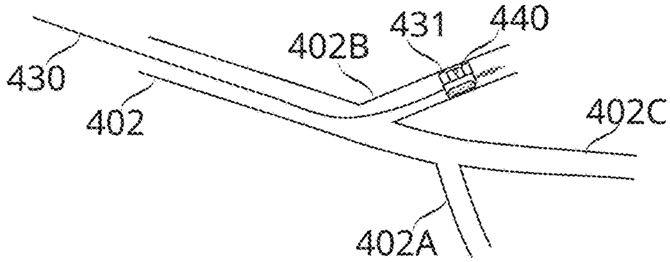
FIG. 4E
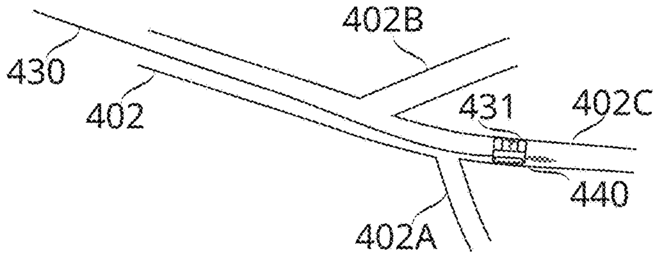
FIG. 4F

PLASMA CONTROL

RELATED APPLICATIONS

This application is a National Phase of PCT Patent Application No. PCT/IL2022/050595 having International filing date of Jun. 3, 2022 which claims the benefit of priority under 35 USC § 119 (e) of U.S. Provisional Patent Application No. 63/196,251 filed on Jun. 3, 2021.

PCT Patent Application No. PCT/IL2022/050595 is also related to co-filed, and co-assigned PCT Patent Application No. PCT/IL2022/050596, filed on Jun. 3, 2022 and entitled "PLASMA AUTOMATED CONTROL".

The contents of the above applications are all incorporated by reference as if fully set forth herein in their entirety.

FIELD AND BACKGROUND OF THE INVENTION

The present invention, in some embodiments thereof, relates to the field of plasma-based medical treatments and more particularly, but not exclusively, to cold plasma-based medical treatment.

Plasma is a general term encompassing compositions of ionized gas, generally including free electrons and ions, as well as neutral atoms and molecules, and often free radicals. Plasma may be produced by electric discharge through gas, causing gas atoms or molecules to be excited and ionize. During the past decade, significant interest in plasma applications has grown. Some applications are based on Dielectric Barrier Discharge (DBD) for generation of the non-thermal plasma of low temperature, or so-called "cold" plasma. Such cold plasma is a low-ionized and non-thermal plasma generated at atmospheric pressure conditions. It has been found that cold plasma can be used for various applications in medicine and industry.

SUMMARY OF THE INVENTION

According to an aspect of some embodiments of the present disclosure, there is provided a system for providing a controlled plasma dosage to a target region of tissue of a subject, the system including: a plasma delivery probe; a motion controller configured to move a plasma plume produced from the plasma delivery probe; and a processor and a memory storing processor instructions which instruct the processor to: access a specification of a total specific dosage specifying a targeted range of effective plasma to be delivered by the plasma delivery probe to sub-regions of the target region of the tissue, instruct the motion controller to move the plasma plume, according to movements planned to deliver the total specific dosage to the target region while the plasma delivery probe operates to provide plasma, receive an indication of a rate of actual plasma delivery, determine that the indicated rate, together with the planned movements, may not produce the specified total specific dosage of plasma for a sub-region of the target region, and adjust operation of the plasma delivery probe so that actually delivered total specific dosage of plasma in the sub-region satisfies the specification of the total specific dosage of plasma.

According to some embodiments of the present disclosure, the processor adjusts operation of the plasma delivery probe by a modification to the planned movements.

According to some embodiments of the present disclosure, the modification to the planned movements includes changing a speed of movement of the plasma delivery probe.

According to some embodiments of the present disclosure, the modification to the planned movements includes changing a planned position of the plasma delivery probe.

According to some embodiments of the present disclosure, the processor receives the indication of the rate of actual plasma delivery from the at least one sensor.

According to some embodiments of the present disclosure, the at least one sensor measures power dissipated by plasma generation.

According to some embodiments of the present disclosure, the at least one sensor includes a temperature sensor.

According to some embodiments of the present disclosure, the at least one sensor includes a spectral emission detector configured to measure spectral emissions from the plasma.

According to some embodiments of the present disclosure, the at least one sensor includes a position sensor configured to measure a current position of the plasma delivery probe.

According to some embodiments of the present disclosure, the planned movements include a plurality of locations within the target region at which movement of the plasma delivery probe pauses while the plasma delivery probe delivers plasma.

According to some embodiments of the present disclosure, the system includes a rigid introducer sized to introduce the plasma delivery probe to the target tissue region, internal to the subject.

According to some embodiments of the present disclosure, the planned movements include at least one of inserting and withdrawing the introducer while plasma is delivered continuously from the plasma delivery probe.

According to some embodiments of the present disclosure, the planned movements comprise a contiguous pathway along which the plasma delivery probe continuously moves while delivering the plasma.

According to some embodiments of the present disclosure, the delivery of the plasma is onto successive contiguous surface regions along the contiguous pathway.

According to some embodiments of the present disclosure, the indication is a measured reduction in the power dissipated by plasma generation, and the operation of the plasma probe is adjusted by moving the plasma delivery probe towards the target region.

According to some embodiments of the present disclosure, the processor selects a distance of the movement towards the target region according to the magnitude of an increase in measured power as the plasma probe is moved toward the target region.

According to some embodiments of the present disclosure, the processor halts movement of the probe towards the target region upon the measured power reaching a substantially constant level.

According to some embodiments of the present disclosure, the indication of the rate of actual plasma delivery includes a measurement of a flow of ionization gas to the plasma plume; and the operation of the plasma delivery probe is adjusted by slowing movement of the plasma delivery probe in response to a decrease in the flow.

According to some embodiments of the present disclosure, the indication of the rate of actual plasma delivery includes a measurement of a flow of ionization gas to the plasma plume; and the operation of the plasma delivery probe is adjusted by withdrawing the plasma delivery probe in response to a decrease in the flow.

According to some embodiments of the present disclosure, the indication of the rate of actual plasma delivery includes a measurement of a temperature in the vicinity of the plasma plume; and the operation of the plasma delivery probe is adjusted by both reducing power to and slowing movement of the plasma delivery probe in response to an increase in temperature.

According to some embodiments of the present disclosure, the indication of the rate of actual plasma delivery includes a mismatch between controller instructions to robotically move the plasma probe and resulting position changes of the plasma probe.

According to some embodiments of the present disclosure, the operation of the plasma delivery probe is adjusted by a modification to the planned movements.

According to some embodiments of the present disclosure, the parameter indicative of the rate of actual plasma delivery indicates a change in distance between the plasma delivery probe and the tissue; and the processor adjusts a speed with which the plasma delivery probe is moved by the controller over a surface of the target region of tissue, based on the parameter.

According to some embodiments of the present disclosure, a specification of the selected dosage is indicative of a cumulative time of plasma exposure.

According to some embodiments of the present disclosure, the specification of the total specific dosage is indicative of a reference power level of the plasma delivery probe.

According to some embodiments of the present disclosure, the planned movements comprise a gross movement pattern upon which finer movement pattern is superimposed; wherein the gross movement pattern alone defines coverage of the target region, and the fine movement pattern superimposes with the gross movement pattern to reduce dosage inconsistency due to non-uniformities in the plasma plume.

According to some embodiments of the present disclosure, the indication of the rate of actual plasma delivery is an indication of a pattern of gaseous flow near the target region of tissue; and operation of the plasma delivery probe is adjusted to modify the pattern of gaseous flow.

According to some embodiments of the present disclosure, the indication is a measurement of temperature, and the operation of the plasma delivery probe is adjusted by modifying its orientation.

According to an aspect of some embodiments of the present disclosure, there is provided a system for providing a controlled plasma dosage to a target region of tissue of a subject, the system including: a plasma delivery probe; a motion controller configured to move a plasma plume produced from the plasma delivery probe; and a processor and a memory storing processor instructions which instruct the processor to: access a specification of a total specific dosage specifying a targeted range of effective plasma to be delivered by the plasma delivery probe to sub-regions of the target region of the tissue, detect movements of the plasma plume, receive an indication of a rate of actual plasma delivery, determine that the indicated rate, together with the detected movements, may not produce the specified total specific dosage of plasma for a sub-region of the target region, and adjust operation of the plasma delivery probe so that actually delivered total specific dosage of plasma in the sub-region satisfies the specification of the total specific dosage of plasma.

According to an aspect of some embodiments of the present disclosure, there is provided a method of controlling a total plasma dosage specifying an acceptable range of total plasma received by each sub-region of the target region, and to be delivered to the target region by a plasma delivery probe, the method including: selecting the target region; generating plasma from the plasma delivery probe; positioning the plasma delivery probe near the target region; and robotically moving the plasma delivery probe to deliver the plasma to the target region, the moving being in a pattern defined according to the selected dosage and at least one input indicative of a rate of plasma delivery from the plasma delivery probe.

According to some embodiments of the present disclosure, the target region is a region of tissue.

According to some embodiments of the present disclosure, the target region is a region of a food item.

According to some embodiments of the present disclosure, the pattern defines a plurality of locations within the target region at which movement of the plasma delivery probe pauses while the plasma delivery probe delivers plasma.

According to some embodiments of the present disclosure, the plasma delivery probe includes a rigid introducer, and including inserting the rigid introducer into the target region to reach, with the delivered plasma, each of the of the plurality of locations.

According to some embodiments of the present disclosure, the method includes robotically moving the plasma delivery probe to direct the delivered plasma onto successive surface regions, each defined by a position of one of the locations.

According to some embodiments of the present disclosure, the pattern includes a contiguous pathway within the target region along which the plasma delivery probe is continuously moved while delivering the plasma.

According to some embodiments of the present disclosure, the plasma delivery probe includes a rigid introducer, and including inserting the rigid introducer into the target region to reach, with the plasma, one end of the contiguous pathway; and then withdrawing the rigid introducer; wherein plasma is delivered continuously as the rigid introducer moves in at least one of the directions of inserting and withdrawing.

According to some embodiments of the present disclosure, the method includes robotically moving the plasma delivery probe to direct the delivered plasma onto successive contiguous surface regions along the contiguous pathway.

According to some embodiments of the present disclosure, the surface regions are lumenal surfaces of a body lumen.

According to some embodiments of the present disclosure, the method includes inserting the plasma delivery probe into the lumen, and then performing the robotically moving.

According to some embodiments of the present disclosure, the method includes measuring the rate of plasma delivery, and adjusting the robotic movement to maintain the selected dosage based on changes in the rate of plasma delivery.

According to some embodiments of the present disclosure, the measuring the rate of plasma delivery includes measuring power dissipated by plasma generation.

According to some embodiments of the present disclosure, adjusting the robotic moving to maintain the selected dose includes changing a speed of movement of the plasma delivery probe.

According to some embodiments of the present disclosure, adjusting the robotic moving to maintain the selected dose includes: measuring power dissipated by plasma generation; and adjusting a position of the plasma delivery probe according to the measuring.

According to some embodiments of the present disclosure, the measuring measures a reduction in the measured power dissipated by plasma generation reduces, and the adjusting includes moving the plasma delivery probe by a distance towards the target region that increases the measured power.

According to some embodiments of the present disclosure, the measured power dissipated by plasma generation reaches a substantially constant level while the plasma delivery probe is being advanced to the target region, and including halting the advance.

According to some embodiments of the present disclosure, the measuring the rate of plasma delivery includes measuring a flow of ionization gas to the plasma plume; and including slowing movement of the plasma delivery probe in response to a decrease in the flow.

According to some embodiments of the present disclosure, the measuring the rate of plasma delivery includes measuring flow of ionization gas to the plasma plume; and including withdrawing the plasma delivery probe in response to a decrease in the flow.

According to some embodiments of the present disclosure, the measuring the rate of plasma delivery includes measuring temperature in the vicinity of the plasma plume; and both reducing power to and slowing movement of the plasma delivery probe in response to an increase in temperature.

According to some embodiments of the present disclosure, the method includes detecting a mismatch between controller instructions to robotically move the plasma probe and resulting position changes of the plasma probe; and adjusting the operating of the plasma delivery probe to maintain the selected dosage.

According to some embodiments of the present disclosure, the method includes detecting a mismatch between controller instructions to robotically move the plasma probe and resulting position changes of the plasma probe; and adjusting the robotic moving to maintain the selected dosage.

According to some embodiments of the present disclosure, the method includes: measuring a parameter indicative of a change in distance between the plasma delivery probe and the target region; and adjusting a speed with which the plasma delivery probe moves over a surface of the target region, based on the measuring.

According to some embodiments of the present disclosure, a specification of the selected dosage is indicative of a cumulative time of plasma exposure.

According to some embodiments of the present disclosure, a specification of the selected dosage is indicative a reference power level of the plasma delivery probe.

According to some embodiments of the present disclosure, the defined pattern includes a gross movement pattern upon which finer movement pattern is superimposed, wherein the gross movement pattern alone defines coverage of the target region, and the fine movement pattern superimposed with the gross movement pattern to reduce dosage inconsistency due to non-uniformities in the plasma plume.

According to some embodiments of the present disclosure, the method includes determining a pattern of gaseous flow near the target region; and adjusting the defined pattern to account for the pattern of gaseous flow.

According to an aspect of some embodiments of the present disclosure, there is provided a method of distributing plasma over a target region, including: introducing at least one ionization gas delivery tube to a body lumen; positioning the at least one ionization gas delivery tube to produce a predefined pattern of ionization gas flow near a surface of the target region; positioning a discharge electrode within the pattern of ionization gas flow at a position wherefrom the ionization gas flow draws plasma from the discharge electrode along the target region; and producing plasma by providing electrical power to the discharge electrode.

According to some embodiments of the present disclosure, the at least one ionization gas delivery tube is positioned separately from the discharge electrode.

According to some embodiments of the present disclosure, the pattern of ionization gas flow includes a vortex, and a center of the vortex is positioned over the target region, with the flow along the surface of the target region being around the center of the vortex.

According to some embodiments of the present disclosure, the pattern of ionization gas flow is induced by positioning of the at least one ionization gas delivery tube near an entrance aperture to the body lumen, and includes a flow of gas directed circumferentially around the body lumen and back to the entrance aperture.

According to some embodiments of the present disclosure, the discharge electrode is positioned near a wall of the body lumen opposite the entrance aperture to the body lumen.

According to an aspect of some embodiments of the present disclosure, there is provided a method of controlling plasma dosage delivered to a target region, including: setting parameters of a plasma generating device; generating plasma using the parameters; delivering the plasma to the target region from a moving plasma delivery probe under robotic control; observing a mismatch between a commanded robotic movement of the plasma delivery probe and an actual movement of the plasma delivery probe; and adjusting the parameters, based on the observed mismatch.

According to some embodiments of the present disclosure, the mismatch is due to hysteresis in the movement response of the plasma delivery probe to robotic actuation.

According to some embodiments of the present disclosure, the mismatch is due to sudden release of a force restraining movement of the plasma delivery probe to robotic actuation.

According to some embodiments of the present disclosure, a change in the mismatch is anticipated, including adjusting the parameters according to the anticipated change in the mismatch, before the change in mismatch occurs.

According to an aspect of some embodiments of the present disclosure, there is provided a method of controlling plasma dosage delivered to the target region, including: setting parameters of a plasma generating device; generating plasma using the parameters; delivering the plasma to the target region from a moving plasma delivery probe under robotic control; observing a mismatch between an expected power level of plasma generation, and a measured power level of plasma generation; and adjusting movement of the plasma delivery probe, based on the observed mismatch.

According to an aspect of some embodiments of the present disclosure, there is provided a system for controlling plasma dosage to tissue, the system including: a plasma delivery probe; a motion controller configured to move plasma generated from the plasma delivery probe; and a processor and a memory storing processor instructions which instruct the processor to command the motion controller to move the plasma to provide sub-regions of the target region with a specified total effective specific dosage of the plasma, based on a rate of plasma delivery from the plasma deliver probe; wherein the processor commands account for spatial non-uniformity of the rate of plasma delivery adjusting the commanded movements to reduce consequent deviation of actually delivered total specific dosage from the specified total effective specific dosage.

According to some embodiments of the present disclosure, the rate of plasma delivery is also adjusted to reduce non-uniformity of actually delivered total specific dosage consequent to the spatial non-uniformity of the rate of plasma delivery.

According to some embodiments of the present disclosure, the pattern of calculated movement is calculated to intersect some sub-regions more than others.

According to some embodiments of the present disclosure, the pattern of calculated movement includes a relatively finer movement pattern superimposed upon a gross movement pattern; wherein the gross movement pattern alone defines coverage of the target region, and the finer movement pattern superimposes with the gross movement pattern, thereby reducing non-uniformity of the specific dosage due to non-uniformities in the plasma plume.

According to some embodiments of the present disclosure, the controller is instructed to move the plasma delivery probe to a plurality of discrete positions from which the plasma is delivered.

According to some embodiments of the present disclosure, the plasma delivery probe includes a rigid introducer, and the controller is instructed to insert the rigid introducer into the target region of tissue to successively reach, with the delivered plasma, each of the of the plurality of discrete locations.

According to some embodiments of the present disclosure, the controller is instructed to move the plasma delivery probe to direct the delivered plasma, successively, onto the discrete surface regions of the target region of tissue.

According to some embodiments of the present disclosure, the controller is instructed to move the plasma delivery probe to along a contiguous pathway within the target region while the plasma delivery probe operates to deliver plasma.

According to some embodiments of the present disclosure, the plasma delivery probe includes a rigid introducer, and the controller is instructed to insert the rigid introducer into the target region of tissue to reach, with the plasma, one end of the contiguous pathway; and then withdraw the rigid introducer; while the plasma delivery probe delivers plasma continuously as the rigid introducer moves in at least one of the directions of inserting and withdrawing.

According to some embodiments of the present disclosure, the controller is instructed to move the plasma delivery probe to direct the delivered plasma onto successive surface regions along the contiguous pathway.

According to some embodiments of the present disclosure, the system comprises at least one sensor configured to measure one or more parameters indicative of the plasma delivery rate; wherein the processor accesses measurements by the sensor; and wherein the processor is instructed to adjust movement the plasma delivery probe by the controller to maintain the specified dosage, based on changes in the plasma delivery rate.

According to some embodiments of the present disclosure, the at least one sensor measures power dissipated by plasma generation as one of the parameters indicative of the plasma delivery rate.

According to some embodiments of the present disclosure, the movement is adjusted to change speed a speed of movement of the plasma delivery probe.

According to some embodiments of the present disclosure, the movement is adjusted to change a position of the plasma delivery probe according to the measured power dissipated by plasma generation.

According to some embodiments of the present disclosure, when the measured power dissipated by plasma generation reduces, the controller moves the plasma delivery probe to a distance from the target region that increases the measured power.

According to some embodiments of the present disclosure, when the measured power dissipated by plasma generation reaches a substantially constant level while the plasma delivery probe is being advanced to the target region, the controller halts the advance.

According to some embodiments of the present disclosure, the at least one sensor measures a flow of ionization gas to the plasma plume as one of the parameters indicative of plasma delivery rate, and the processor is instructed to adjust movement of the plasma delivery probe in response to a decrease in flow.

According to some embodiments of the present disclosure, the processor slows movement of the plasma delivery probe in response to a decrease in flow.

According to some embodiments of the present disclosure, the processor withdraws the plasma delivery probe proximally in response to a decrease in flow.

According to some embodiments of the present disclosure, the at least one sensor measures temperature in the vicinity of the plasma plume, and the processor is instructed to reduce power to and slow movement of the plasma delivery probe in response to an increase in temperature.

According to some embodiments of the present disclosure, the processor is instructed to access position information indicative of potential mismatch between controller instructions to robotically move the plasma probe and actual plasma probe position; and instructed to adjust operation of the plasma delivery probe to maintain the selected dosage, based on the position information indicative of the mismatch.

According to some embodiments of the present disclosure, the processor is instructed to access position information indicative of potential mismatch between controller instructions to robotically move the plasma probe and actual plasma probe position; and instructed to perform the robotic moving to maintain the selected dosage, based on the position information indicative of the mismatch.

According to some embodiments of the present disclosure, the mismatch is due to hysteresis in a response of the plasma delivery probe to the controller.

According to some embodiments of the present disclosure, the mismatch is due to uncontrolled release of torsion in a response of the plasma delivery probe to the controller.

According to some embodiments of the present disclosure, the controller moves the plasma delivery probe by advancing or withdrawing it along a longitudinal axis of the plasma delivery probe.

According to some embodiments of the present disclosure, the controller moves the plasma delivery probe by rotating it around a longitudinal axis of the plasma delivery probe.

According to some embodiments of the present disclosure, the controller moves the plasma delivery probe by adjusting a spacer that spaces the plasma delivery probe relative to an adjacent contact of the spacer with a wall.

According to some embodiments of the present disclosure, the controller moves the plasma delivery probe by swiveling the plasma delivery probe.

According to some embodiments of the present disclosure, the controller moves the plasma delivery probe by lateral translation of a proximal portion of the plasma delivery probe.

According to an aspect of some embodiments of the present disclosure, there is provided a system for mapping 3-D structure of a surface, including: a motion controller; a plasma probe; a processor and a memory storing processor instructions which instruct the processor to: instruct the controller to move the plasma delivery probe while the plasma delivery probe operates to provide a plasma plume, access data indicative of power levels dissipated into the plasma plume, calculate distances to a target contacted by the plasma plume, based on the power levels, and generate a 3-D map of the target, based on offsetting from positions of the plasma probe by the calculated distances to the target contacted by the plasma plume.

According to some embodiments of the present disclosure, the instructions instruct the processor to prepare the 3-D map of the target as an image and present it on the display.

According to some embodiments of the present disclosure, the 3-D map of the target is used as a basis for adjusting movements of the plasma delivery probe.

According to some embodiments of the present disclosure, the plasma is cold plasma used for non-ablative treatment of a medical condition at the target.

According to an aspect of some embodiments of the present disclosure, there is provided a method of controlling plasma dosage delivered to tissue, including: setting parameters of a plasma generating device; generating plasma using the parameters; delivering the plasma to the tissue from a moving plasma delivery probe under robotic control; observing a mismatch between an expected power level of plasma generation, and a measured power level of plasma generation; and adjusting movement of the plasma delivery probe, based on the observed mismatch.

According to an aspect of some embodiments of the present disclosure, there is provided a method of controlling plasma dosage delivered to a target region, the method including: selecting the target region; selecting a total specific dosage (1) specifying an acceptable range of total plasma received by each sub-region of the target region, and (2) to be delivered to the target region by a plasma delivery probe; generating plasma from the plasma delivery probe; positioning the plasma delivery probe near the target region to deliver plasma in a pattern having a spatially non-uniform instantaneous rate of plasma delivery to regions receiving plasma simultaneously; and robotically moving the plasma delivery probe to deliver the plasma to the target region, the moving being in a pattern defined according to the selected dosage; wherein the robotic movement is adjusted to reduce deviation of actually delivered total specific dosage from the specification of total specific dosage, due to the spatial non-uniformity of the instantaneous rate of plasma delivery.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in method and/or by system are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry. It should be understood that there is no particular limitation of the term "processor" to any particular arrangement and/or packaging of computer circuitry. A processor may be implemented, for example, as a single computer chip, as a plurality of computer chips (including computer chips distributed among a plurality of enclosures), as a combination of digital and analog processing circuits, or in another configuration.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable medium to receive instructions and/or data therefrom, process them, and/or store processing results in the same or another computer readable medium. The processing performed (optionally on the data) is specified by the instructions, with the effect that the processor operates according to the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIG. 4A schematically represents a plasma control unit controlled in conjunction with a probe positioning system to provide plasma treatment from within a lumen, according to some embodiments of the present disclosure;

FIGS. 4B-4C schematically represent a plasma delivery probe equipped with a deployable docking mechanism, and configured to deliver plasma from plasma generating module in one or both of a direction lateral to a longitudinal axis of the probe (FIG. 4B), and a direction along the longitudinal axis of the probe (FIG. 4C); according to some embodiments of the present disclosure;

FIGS. 4D-4F schematically represent positioning of plasma generating module within a branched lumenal structure, according to some embodiments of the present disclosure;

DESCRIPTION OF SPECIFIC EMBODIMENTS OF THE INVENTION

Figure 1A:
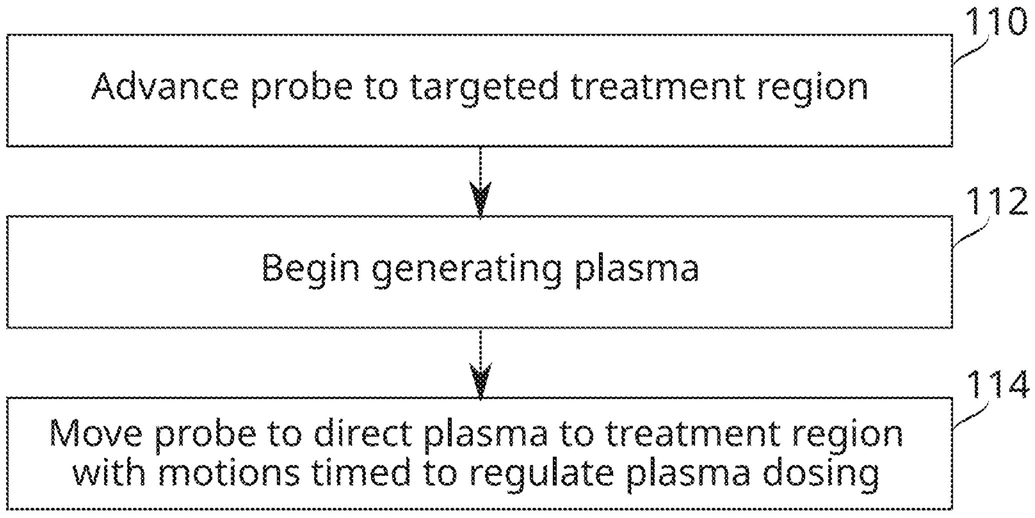
FIG. 1A schematically represents a method of controlling plasma dosage delivered to tissue, according to some embodiments of the present disclosure.

The present invention, in some embodiments thereof, relates to the field of plasma-based medical treatments and more particularly, but not exclusively, to cold plasma-based medical treatment.

Overview

A broad aspect of some embodiments of the present disclosure relates to the use of reactive species in medical plasma to treat medical conditions. In some preferred embodiments, this involves providing cold (non-thermal) plasma to living tissue under conditions of medically acceptable temperature, safety, and sterility (i.e., the devices are medical-grade plasma generating devices); and in particular at a temperature which remains below a threshold of thermal injury (e.g., below 50° C.) and/or protein denaturation (e.g., below 40° C.).

Potentially, the cold plasma has therapeutic effects, e.g., it may act to destroy and/or trigger the destruction of tumor cells and/or pathogens such as viral particles, bacteria, fungi, and/or prions.

A suggested mechanism of therapeutic action involves sensitivity to free radicals. In some cases there may be a differential sensitivity; i.e., a targeted tumor and/or pathogen is more sensitive to free radicals than nearby healthy tissue. Treatment effects potentially depend on interactions between parameters of the target (e.g., surrounding fluid, target size, and/or target type) and parameters of the plasma delivered (e.g., generated ionized species, their concentrations and/or ratios). Parameters of the plasma delivered in turn potentially are affected by parameters of the generation of the plasma (e.g., ionizing medium composition and/or electrical parameters), and parameters of the plasm plume itself (e.g., geometry, containment, flow, and/or quenching).

Parameters of plasma generation which produce these therapeutic effects potentially vary significantly across different plasma generator designs, ionization gas used as a medium, contents of plasma generated, environment, tumor/pathogen size, and/or tumor/pathogen type. Accordingly, it is a potential advantage for a plasma delivery device to be operable under a range of operating parameters.

Herein, references to "plasma" and "plasma plume" refer more specifically to cold plasma (e.g., plasma at a temperature of 50° C. or less, and preferably delivered at a temperature less than body temperature, e.g., within a range of about 20° C.-30° C.). The cold plasma is generally delivered under conditions of approximately atmospheric pressure, and accordingly also referred to as "cold atmospheric plasma" or CAP. Equivalently, such plasma may be referred to as "non-thermal atmospheric plasma" (NTAP).

The plasma plume is generated from a supply of "ionization gas", which optionally comprises any suitable mix of atomic and/or molecular species (including a single species) which can be ionized to generate the cold plasma. Typical ionization gas mixtures include one or more noble gasses optionally mixed with other species, for example, molecules of nitrogen, oxygen, and/or water.

The tissue target to which cold plasma is delivered, in some embodiments, is internal to a living body. Optionally, the target is outside a living body, and optionally the target is not a portion of a living human body. For example, the target is optionally a calibration target, e.g., a target instrumented to characterize what plasma is produced at different settings of the plasma delivery device, optionally including different parameter settings of the plasma delivery tip; for example: different dielectric barrier thicknesses, different gas delivery lumen diameters, and/or different discharge electrode widths. Additionally or alternatively, the target is an assay target; e.g., a target of an in vitro and/or ex vivo assay of cold plasma effects (e.g., under conditions of different parameter settings of the plasma delivery tip) on one or more types of, for example: tumor cells, pathogen cells, infectious particles (viruses or prions), healthy cells, and/or tissue samples.

Cold plasma is generated in a non-equilibrium state, and its ionization state rapidly decays as charged species interact with each other, with other species in the ionization gas, and/or with the environment.

In some embodiments, a plume of cold plasma (of, e.g., about 1-20 mm in length) is generated from a high-voltage discharge electrode operated within an ionization gas environment created near the target. A potential advantage of generating plasma is such close proximity to its target is reduction of plasma degradation due, e.g., to interaction with conduit walls. Characteristic of its non-equilibrium state, cold plasma is low-ionized. Ionization is estimated, for some cold plasmas, as being (within a factor of about 10) about a part per million and/or $10^{11}$-$10^{13}$ electrons/$cm^3$. The generated plasma is carried on toward the target by flowing of the ionization gas.

Body-internal access allowing plasma application to the tissue target is optionally facilitated by the use of a relatively small-diameter (e.g., 5 mm or less) distal tip of a plasma generation device (at which tip the plasma is also generated).

The small-diameter plasma-generating tip itself may be introduced to the target, for example, using a catheter sheath and/or endoscope working channel. The plasma-generating tip is also referred to herein equivalently as a "plasma generating probe", "plasma delivery probe", "plasma probe", or simply as a "probe".

Plasma generation, in some embodiments of the present disclosure, comprises delivering electrical power into a high-voltage gradient electrical field, through a portion of which flows a gas comprising one or more atomic and/or molecular species susceptible to ionization. In brief, the steep voltage gradient of the electrical field tears atoms apart into ions and freed electrons. This can in turn generate a cascading effect as high-energy freed electrons transfer portions of their energy to other, still-bound, electrons, freeing them as well. Freed electrons move at a high temperature (potentially several thousand degrees Kelvin); however, they provide very little of the plasma's thermal mass. The plasma is considered "cold" when the much heavier atomic ions themselves remain at about room temperature (moving relatively slowly). Typical targets for cold plasma generation in medical applications are to maintain the bulk plasma temperature at 40° C. or less (e.g., below protein denaturation temperatures), or 50° C. or less. In some embodiments of the present disclosure, plasma temperature is less than body temperature, and optionally room-temperature, for example, in a range of 20-35° C., and optionally in a range of about 24-25° C. This thermal condition may be enhanced, for example, by removing heat from the system fast enough to overcome the heating effects of input electrical power. One way of doing this is to maintain continuous flow of the supply of the ionization gas (which thus becomes its own coolant). In some embodiments, there is also provision for removing waste ionization gas.

Apart from use in treating disease, other applications for cold plasma have been described, including use as an antimicrobial (sanitizing) treatment in the food industry. Where the characteristics (e.g., flavors and/or textures) of a food item (particularly high-value food items) may be adversely affected by standard preservation techniques, cold plasma offers potential advantages for extending the period of time that the food item can be left in a relatively unmodified state, e.g., to extend available shipping and/or storage times. It is a potential advantage to be able to control plasma delivery in such cases, since, for example, the item itself may be irregular in shape, there may be efficiency and/or quality advantages to avoiding excess dosing, and yet a minimum level of dosing may be set as a process requirement.

An aspect of some embodiments of the present disclosure relates to robotic control of probe positioning to regulate the administration of plasma dosages to tissue, according to some embodiments of the present disclosure.

Cold plasma has the potential to treat disease, for example by exploiting particular sensitivities of diseased tissue to reactive species found within the plasma itself and/or generated upon contact with the plasma. Delivered with the use of a small diameter probe (flexible or rigid), plasma delivery can also be delivered with high spatial precision.

Furthermore—and unusually for a dosing material—this precision is assisted by the short-lived nature of the reactive species that the plasma contains and generates. Together with these potential advantages for precision targeting, however, comes the problem of ensuring that all parts of a treatment target receive appropriate plasma exposure (proper plasma dosing). Mere flooding of a targeted area with plasma is typically insufficient.

In some embodiments of the present disclosure, the cold plasma is also unlike other dosing substances in that it is actually being generated at the site of delivery. The plasma is generated using an electrical voltage applied to a flow of ionizing gas. Exactly what is being generated at any given moment can be affected by anything that interacts either with the flow of gas (e.g., a momentary blockage as a catheter tip is pressed up against a target surface), or with the delivery of electrical voltage (e.g., a momentary contact with fluid). Furthermore, the composition of generated plasma evolves quickly as it re-equilibrates, so that even the distance between the plasma generation site and the site of targeted treatment can become a factor affecting proper dosing.

The reactive species of plasma (and/or generated by plasma) may travel differently depending on the environmental conditions within which the plasma is delivered. For example, within an ionization gas-filled urinary bladder, plasma species are quickly carried away by the flow of gas, and potentially spread over a large area from a restricted site of origin. Whether the ionization gas is flowing or static, the rate of diffusion in gas may also be relatively high. Inside the volume of a tissue, species are substantially restricted to movement by diffusion. A liquid environment may be intermediate in distance dependency between those two cases. These examples illustrate how a pattern of movement (also referred to herein as "planned movements") of the plasma-generating source may be set variably depending on the flow and diffusiveness which are allowed in the environment of the source. The "movements" (including "planned movements") may be considered to apply to the plasma itself, as there may be aspects of how it is controlled that are realized through manipulation of degrees of freedom that don't actually move the probe itself; for example, the pressure of ionization gas may control the longitudinal extent of a plasma plume.

It furthermore be noted that with respect to these variables, appropriate parameters for different environments may be determined by observation of outcomes in in vitro or in vivo tests which model the target environment. probe dwell times and/or rates of movement. Ionization gas flow rate is optionally selected from within a range of about 0.1 L/min to about 10 L/min. Optionally, duty cycle of plasma generation is adjusted, for example, within a range of about 10% 2.5 to 100%. Movements scanning across a treatment target may range, for example, from about 0.1-10 mm/sec.

More theoretically-based models optionally factor in estimates of factors such as reactive species lifetimes, diffusion/flow rates and/or volume dilution factors.

Some proposed mechanisms of the action of plasma treatment include the conversion of materials already at the site of treatment into reactive species (e.g., free radicals). Thus, for example, a wet target may generate more OH reactive species than a dry one as plasma ions interact with the water. The ionization gas from which the plasma is made may itself be a drying gas, so the concentration of generated free OH reactive species can alter over time.

Finally, it may be preferable, in some embodiments of the present disclosure, to administer plasma treatments using nearest access to a target available from the body's natural passageways (e.g., sinuses, urinary tract, gastrointestinal tract, vasculature, heart chambers, and/or brain ventricles), rather than attempt to invade the target physically. This may allow avoiding potentially traumatic direct invasion of target tissue, as along as dwell times can be increased enough to allow a therapeutic amount of plasma to be delivered that to the target from an adjacent location.

These considerations illustrate that effective plasma treatment may depend not just on reaching a target with a plasma delivery probe, but also on details of a spatiotemporal pattern of movement of the plasma delivery probe as it is operated within and/or adjacent to the target.

Herein, a "dose of plasma" should be understood to relate to a total amount of plasma-generated reactive species delivered per unit of tissue area or tissue volume in a zone which receives the plasma. This is also referred to herein as the "specific dosage", wherein the dosage is delivered per "unit" of an overall target region, however the unit is defined. The unit may be defined straightforwardly in terms of surface area, volume, or weight. Optionally (e.g., in a structurally inhomogeneous region), the unit is further adjusted, e.g., for dosage-relevant dynamic and/or structural properties such as a local diffusion constant, flow rate (e.g., of blood), diffusion barrier thickness, or another property.

In some embodiments, the specific dosage is specified in terms of expected (e.g., calibrated) effects, referred to herein as "effective plasma". In some embodiments, the specification of "effective plasma" is in a 1:1 relationship with actual plasma, at least insofar as actual plasma is known from measurements and/or device operating parameters. Optionally, the specific dosage is weighted according to estimated non-linearities in effects. For example, a period of higher-intensity administration of reactive species may be more heavily weighted than a period of lower-intensity administration, even if the total administration of reactive species (e.g, in moles per target region unit) is the same. Accordingly, a definition of specific dosage in terms of effective plasma optionally includes allowance for non-linearities in treatment effects.

Unless otherwise stated, the specific dosage is considered herein to be a "total" dosage; that is, a (potentially variable) rate of plasma delivery may be integrated during a period of treatment to obtain the specific dosage. Accordingly, the phrase "total specific dosage" may be used interchangeably with the phrase "specific dosage". It is a goal, in some embodiments of the present disclosure, to provide a specific dosage of plasma which is uniform (within some tolerance range) across a treated area. In some embodiments, the specific dosage is deliberately varied over a region; e.g., higher in regions which are already "overwhelmed" by a disease, and lower in regions where a balance between preserving healthy tissue and treating the disease is to be maintained. Herein, the phrase "specific dosage" should be understood in the sense of dosage per unit, and not in the sense of "particular dosage", unless otherwise stated explicitly. The phrase "unit specific dosage" may also be used herein. This phrase should be understood as interchangeable with the phrase "specific dosage" as just defined.

Since metering of reactive species as such may be unavailable or impractical, the dosing is optionally expressed in terms of parameters governing the production of plasma, parameters varying according to how much plasma is actually produced, and/or measurements of a characteristic of the plasma.

The process of dose delivery as such is not necessarily exact, precise, or uniform, albeit embodiments of the present disclosure include features which are operable to help control dose delivery. Herein, a targeted or selected dosage should be understood to be delivered as substantially as targeted or selected when the conditions defining the targeted or selected dosage are met within some acceptable range. The acceptable range depends on the particular application, e.g., an amount of variation deemed acceptable based on previous performance data for that application.

The range may be defined, for example, as delivery within a factor of two, delivery within a factor of ±25%, or within another range relative to some specified key dosage value. Optionally, the extremes of the acceptable range are specified separately—e.g., a lower value considered high enough to produce a treatment effect, and an upper value low enough to prevent damage to healthy tissue. Other factors such as an acceptable level of dose non-uniformity may also be part of the dosage definition. For example, a dose of plasma may be defined (e.g., with respect to a particular probe and system configuration) in terms of a range between minimum and maximum values of energy dissipated in plasma generation per unit area of surface treated, with a uniformity such that at least, e.g., 90% of the treated surface receives energy within that range. A range provided to define a specific dosage may be a range of effective plasma delivery (i.e., optionally weighted for estimated effectiveness of plasma delivery, beyond the raw amount of delivered plasma as such).

Herein, the expression "unit of tissue" may refer to a unit defined in any terms suitable to the dosing situation; typically as an area or a volume. The reactive species may be those which are directly generated with the plasma. Optionally reactive species generated secondarily (e.g., by interaction of plasma with other gasses and/or liquids) are also taken into account in the dosing specification. Distribution through tissue is not necessarily uniform, so that a "unit of tissue" may be more particularly understood (and optionally explicitly defined) as, e.g., a unit of tissue at the center of the plasma plume, and/or a unit of tissue within 1 mm of the plasma contact surface. It may be assumed, in some embodiments, that tissue nearby tissue meeting this "ideal" specification can be taken as receiving a safe and sufficient dosage of plasma when the idealized dosing specification is satisfied. In some embodiments, patterns of movement and/or positioning are selected to ensure that all targeted tissue is sufficiently "nearby" tissue receiving the targeted dose.

Since plasma is short-lived (e.g., cold plasma is in a non-equilibrium state even from its moment of generation), the zone receiving plasma is localized around tissue regions directly contacted by the plasma plume. It is not limited to just regions directly contacted by the plasma plume, however. It is noted, for example, that the small-molecular weight reactive species present in plasma and/or in plasma's reaction products with other species are particularly subject to diffusion. As an indication of scales involved: in some embodiments, the plasma plume contacts a planar tissue surface in a roughly circular region having a diameter of 1-5 mm. The plume length may be, for example, in a range between about 0.5 and 10 mm.

In one method of calculation, the "amount" of plasma-generated reactive species delivered is expressed in the unit of moles per unit of tissue. Then actual dosing can be calculated by estimating the moles per unit time per unit surface/volume delivered, and selecting an integration time long enough to equal the targeted amount. However, dosing amount is not necessarily calculated through the use of fundamental units in this fashion.

For example, there may be available observations of a dose-response curve as a function of power delivered to a particular plasma probe, and/or as a function of time during which that power is delivered. Where only one of these dose response curves is available, it is optionally assumed that the other axis is simply a linear function of its independent variable. For example, for a given power dissipated in plasma generation, dosing may be assumed to increase linearly as a function of time. Conversely, for a given time of plasma exposure, dosing may be usefully assumed to increase linearly as a function of power dissipated into the generation of plasma.

Other parameters besides power and time may be relevant to dosing. Examples include: plasma plume dispersal (itself influenced by factors such as probe geometry, the surrounding volume of free space and/or gas movements), ionization gas flow rate (e.g., flow rate near the discharge electrode), specification of the gas flow mixture, presences and concentrations of species which the plasma plume activates secondarily into reactive species, and rate of diffusion of reactive species into target tissue. Dosing is optionally calculated using through a relationship with one or more observable measurements; for example, the magnitude of a one or more spectral emission peaks of the plasma or power output.

Optionally, dosing amount is calculated using modeled considerations: e.g., dynamics of plasma flow, plume temperature, diffusion constants of reactive species in tissue, and/or time constants of reactive species decay.

In some embodiments of the present disclosure, movement and/or positioning of a plasma delivery probe is used to control exposure time. This may result in a dosing specification which is expressed using a unit of velocity: for example the specification of dosing amount may be expressed in watts (of power dissipated into plasma production) times seconds per millimeter of probe movement relative to a targeted region Although this is optionally simplified by unit analysis, e.g., to joules per millimeter, the involvement of a time factor may still be understood by recognizing, e.g., that the "millimeter" is a millimeter of movement (which necessarily occurs through time), and/or that the joules are not delivered all at once, but rather using a probe operating with a particular power level in watts.

Conversely, power adjustment may be performed in view of actual movement of a plasma plume over a target. A plasma plume may be observed as it it scanned (either automatically or manually) over a target, optionally repeatedly. As estimated effective plasma exposure approaches and/or reaches a targeted total specific dosage in one or more sub-regions of the target, plasma generation may be stopped or attenuated dynamically as plasma production is directed again toward any of the one or more sub-regions of the target.

It should be noted that non-linear effects of dose concentration are not excluded from consideration as part of a dosing specification. For example, it is not excluded that certain therapeutic effects may depend in part on a peak concentration of reactive species, and not just on the total amount of reactive species delivered. Where such non-linearities may be known or suspected to exist, calculations related to dosing control (e.g., via control of movement and/or plasma power delivery) are optionally adjusted accordingly.

In some embodiments, inhomogeneities which are difficult to calculate precisely (e.g., fall-off effects of dosing as a function of distance from the site of plasma contact) are effectively ignored in the dosing specification itself. This may be valid, for example, if a certain dose amount is known from experimentation to be useful, such that inhomogeneity need not be taken into account.

Nevertheless, it may be useful to compensate for inhomogeneity in plasma distribution by designing patterns of plasma-delivering movement which in one way or another "smooth it out". This may improve matching of a dosing specification derived from averages (e.g., average reactive species concentration within the plasma plume) to the expected result at all relevant portions of the target tissue.

One way of decreasing inhomogeneity is to design patterns which cover an area (or volume) of treatment-targeted tissue via a path which is longer than the dimensions of the plasma plume itself require. For example, a pattern comprising parallel tracks can comprise more (and more closely spaced) tracks than are necessary simply to ensure adjacent or singly-overlapping contact of directly treated areas. Another method is to design tracks with a general overall direction extending between two points travel between them along a non-straight path, e.g., a path with loops and/or oscillations.

In some embodiments of the present disclosure, robotically controlled movement patterns are used to help ensure that an appropriate spatiotemporal pattern of the plasma delivery probe is generated. Particularizing from automatic positioning control (and remote positioning control) more generally, the robotically controlled movement patterns described herein are structured not just to bring a plasma delivery probe to particular locations, but to bring the probe to those locations in a pattern of movement which takes into account plasma generating and/or delivery properties of the probe, with the result that a targeted dosage of plasma is delivered.

Two main categories of these robotically controlled movement patterns are zone-based, and scanning-based.

In a zone-based pattern, the target is conceptually divided into a plurality of overlapping zones. The movement pattern is selected to sequentially insert the plasma delivery probe to an approximately central location of each zone, and deliver plasma for a period long enough that the plasma's dosing effects reach the edges of each zone. If more than one probe is available, simultaneous zone treatments are optionally performed. Optionally, effects of diminished treatment effects in regions near zone edges are mitigated by including those regions in more than one zone, to produce cumulative dosing. Purely zone-based patterns have the potential advantage of simplicity (e.g., allowing the positioning tool to remain static while plasma is generated), but may tend to produce a pattern of treatment delivery which is somewhat uneven ("patchy").

In a scanning-based pattern, the target is dosed while the plasma delivery probe is in motion. The motion may be a one-dimensional motion (e.g., as a probe moves along a narrow body lumen, or follows along an introducer track), or a two- or three-dimensional motion (e.g., as a probe is scanned across a body lumen surface or other surface). Treatment in three solid dimensions is not entirely excluded, but for solid targets, it may be confined to movement along a plurality of effectively single-axis tracks.

Combinations of zone-based and scanning-based movement patterns are not excluded, for example, a scanning pattern which also pauses at its extremes of motion to expand the overall range of the treated area. In general, the plasma dose any given region receives may be understood as a time-integration of a function which increases inversely with the moment-by-moment distance of the region from the plasma probe's plasma delivery site. The goal of the movement pattern is to ensure that every targeted area receives a treatment-level dose of plasma. This function is optionally modulated by estimated rates of diffusion, dilution, decay, and/or flow of reactive plasma species and/or species generated secondarily upon exposure to plasma.

It may be noted that with respect to plasma dosing there are two basic loci of device control that can be exercised within a given environment, optionally varied separately or together. One is the spatiotemporal pattern of probe movement itself. The other is the rate or intensity of plasma generation. As a third locus: in particularly free-moving environments (e.g., gas-filled body lumens), parameters of plasma generation can also act as a kind of "motion" parameter, insofar as the rate of flow affects the dispersal distance, and/or direction of generated plasma.

Temperature can interact any of these loci of device control, for example as described in relation to the next aspect.

An aspect of some embodiments of the present disclosure relates to feedback-driven adjustment to regulate the robotically controlled administration of plasma dosages within intrabody spaces, according to some embodiments of the present disclosure.

Plasma generation may be subject to variability, for example as may result from interactions with the environment by a plasma generating probe.

In one example, the amount of power which a plasma generating site is able to convert into plasma may increase (up to its rated power) according to a distance from the target. Environmental confines, however, may limit this distance, limit power delivered into the generation of plasma, and correspondingly lowering the instantaneous dosage of plasma that is delivered. To compensate, in some embodiments of the present disclosure, speed of movement is decreased and/or dwell time of the probe is increased to maintain a targeted dosage level. In some embodiments, such changes in motion pattern are performed automatically by a robotic motion controller in response to calculations based on power level feedback indicating that effective power delivery to the plasma is reduced.

In another example, the flow of ionization gas past a plasma generating site of a plasma delivery probe may potentially change due to a factor such as blockage by tissue, and/or changes in pressure. This may affect dosing by reducing the amount of plasma formed, or the amount which reaches tissue before reactive species decay. By monitoring one or both of pressure and flow rate, an estimate of how dosing is being affected (e.g., reduced) by gas flow can be made, and movements of the probe adjusted to compensate.

Additionally or alternatively, and in situations wherein the target configuration allows it, the robotic movement of the probe may be adjusted via feedback to maintain an optimal distance to the target. This may be used, for example, in embodiments where there is enough clearance that the probe can be set at a selectable distance from the target (e.g., within a range of 3-15 mm, or another range). This type of clearance applies, for example, to treatments applied to inner surfaces of hollow body parts such as bladder, intestine, or lung airways; or even blood vessels if provision is made to evacuate liquid from the treated area, e.g., using balloon blockers to isolate a particular vascular segment (liquid exclusion may also be useful in some lung airway situations). For example, when power delivery is sensed as being below an optimal level, the probe is optionally moved closer to the tissue, increasing the external impedance and thereby increasing overall power delivery. To avoid moving too far away from the target tissue, the movement can be controlled so that the plasma plume length remains within the range to which power fluctuations are sensitive.

In some embodiments, sensed impairment of ionization gas flow is used as feedback to guide withdrawal, e.g., of a plasma probe, or of a plasma probe inserted along an introducer lumen, until enough clearance is restored that the flow of ionization gas can resume.

In some embodiments, feedback control uses temperature sensing as a source of feedback data, optionally, in conjunction with one or more other sensing modalities such as of power level and/or gas flow. While a higher power level may be desirable for purposes of giving a plasma dose more rapidly, it is also important to remain within safe operating parameters, e.g., of temperature. Accordingly, an elevated temperature at the probe may be used as an indication that the power level should be reduced (reducing heat dissipation requirements), and/or that the rate of gas flow should be increased (increasing heat dissipation into the flow of gas). Power can be controlled directly at the source of electrical power generation, and/or by movements which affect the plasma plume length (with consequent effects on power delivery, as already described). Gas flow can be controlled, for example, by regulation of the source, and/or by regulation of a rate at which pressure build up from supplied gas is vented. Since such adjustments may in turn affect the dosing rate, there are also, in some embodiments, compensating changes in the control of automated movements of a plasma delivering probe—e.g., to decrease a rate of scanning movements, and/or increase a dwell time in a certain location.

An aspect of some embodiments of the present disclosure relates to mapping 3-D structures using plasma power feedback information. In some embodiments of the present disclosure, plasma power rises or falls as a distance between a plasma probe and the surface changes. Accordingly, knowing the plasma power provides information allowing the depth position of the surface impinged on by the plasma. This information can be calibrated, for example, by generating a power-to-distance curve for the probe under its intended operating conditions.

During a procedure: knowing the position of a probe delivering the power (e.g., as tracked by a robotic actuation controller), depth-to-surface information calibrated from power readings can be added as an offset, resulting in a mapping of the surface as the probe is moved over it.

In some embodiments, the map is used intra-procedurally, to assist in guiding dosing. For example, edges of a polyp are mapped, and probe movements targeted at guiding plasma into partially protected regions sheltered by overhang planned accordingly. This has the potential advantage of helping to overcome "plasma shadows" (e.g., near the stalk of a pedunculated polyp) which might otherwise prevent plasma from reaching all of a targeted region.

In some embodiments, the map is used as a record of the procedure, for example, to provide a baseline (during a first procedure) which allows estimating (e.g., during a later procedure) changes of the target region such as progress in remission of a growth, and/or to confirm that a whole extent of the targeted area was treated.

An aspect of some embodiments of the present disclosure relates to the superimposition of finer movements on grosser movements as a plasma delivery probe is guided to direct plasma plume onto a target of treatment.

Plasma plumes are potentially non-uniform in their spatial characteristics. For example, a hot spot (thermally hot, or "hot" in the sense of delivering a relatively large amount of reactive species or plasma energy) may be located near the center of the plume, and/or near its circumference. Elsewhere, a region of relatively weak plasma generation and/or delivery may be present.

These non-uniformities (and any resulting spatial non-uniformity in the instantaneous rate of plasma delivery to the region contacted by a plasma plume—the region of non-zero plasma delivery) may be difficult to calculate in a given treatment situation, e.g., due to particulars of the conditions of plasma delivery in a confined space, and/or of non-linearities in dosing response.

In some embodiments of the present disclosure, this is addressed by superimposing smaller movements on larger movements. The larger movements, in effect, control the surface area which receives treatment. The smaller movements potentially even out plasma delivery so that each small area is more consistently dosed.

Keeping the probe in constant motion may also mitigate thermal heating at hot spots, by spreading hot spot energy over a larger area.

The smaller movements imposed on a basic track pattern can comprise, for example, sinusoidal, square, triangular, sawtooth, and/or another shape. In some embodiments, the smaller movements are looping. The basic track pattern itself can be any suitable shape which covers an area: straight-line rastering (continuous or interrupted), one or more spirals, concentric circles, or another pattern.

The smaller movements superimposed on larger movements are optionally modulated as part of feedback-driven control of plasma dosing. For example, dosing can be adjusted via motion control by adjusting the fine-movement oscillation relative to the speed of gross movement along a track (more or less oscillations or loops per millimeter of overall movement, for example).

An aspect of some embodiments of the present disclosure relates to the control of ionization gas flow within a lumenal space to help control plasma dosing of structures within the lumenal space. In some embodiments, plasma is generated by filling a space with ionization gas, and then powering a discharge electrode within that space. If the ionization gas is in motion, the plasma generated will be carried along by its flow. Near lumenal walls, flow will tend to orient parallel to the wall. Flow can be controlled by the positioning of gas inlet and/or outlet apertures. In some embodiments, flow is generated near the discharge electrode by placing inlet and outlet on either side of the electrode, resulting in a predictable flow velocity experienced by generated plasma. In some embodiments, a global pattern of flow is generated, for example, a vortex. In some regions (e.g., of a vortex or near where stream of gas deflects due to blockage by a tissue surface), there may be a fast flow which has the potential advantage of spreading generated plasma species over a larger area. This potentially reduces treatment time and/or increasing treatment efficacy. In some embodiments, regions near an axis of vortical flow have the potential advantage of spreading plasma out while also confining it to a selected region centered approximately on the axis.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Methods of Controlling Plasma Dosage

Figure 1B:
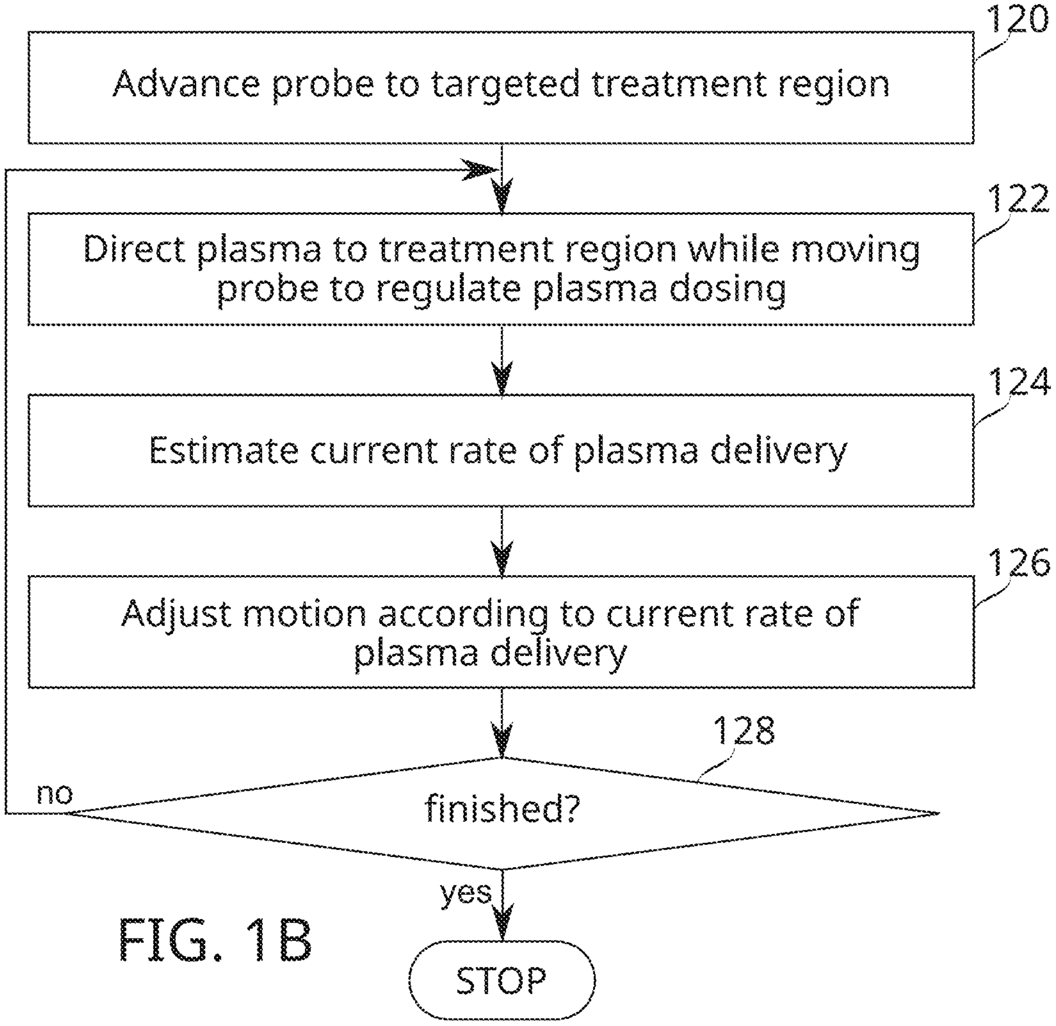
FIGS. 1B-1C schematically represent feedback-controlled methods of controlling plasma dosage delivered to tissue, according to some embodiments of the present disclosure.
Figure 1C:
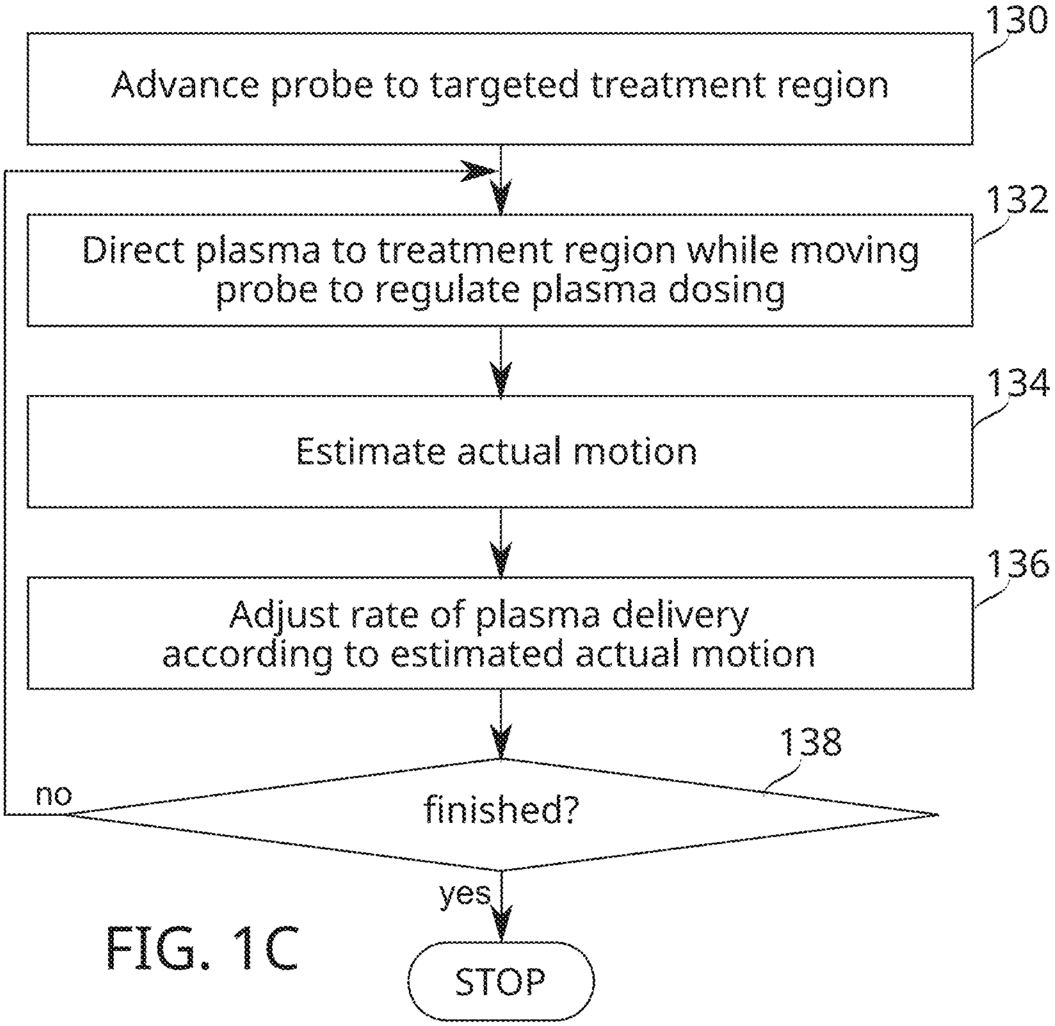

Reference is now made to FIG. 1A, which schematically represents a method of controlling plasma dosage delivered to tissue, according to some embodiments of the present disclosure. Reference is also made to FIGS. 1B-1C, which schematically represent feedback-controlled methods of controlling plasma dosage delivered to tissue, according to some embodiments of the present disclosure.

At blocks 110, 120, 130 (FIGS. 1A-1C), in some embodiments, a probe is advanced to a targeted treatment region. The targeted treatment region is optionally a region of external or internal tissue. The target treatment region is optionally buried at least partially within the volume of a tissue, and/or exposed on a surface (external or internal surface, e.g., an internal lumenal surface). In some preferred embodiments of the present disclosure, the target region is internally accessed, e.g., via a body lumen, needle puncture, and/or endoscopic access. Such probes tend to be thin (e.g., 5 mm in diameter or less). They may be, for example needle-like probes—stiff, and suitable for sharp penetration of tissue. Alternatively, they a probe may comprise a one or more flexible tubes, suitable for insertion through long body lumens alone, through the working channel of another device such as an endoscope or catheter. Plasma generation may be performed by using components inserted separately on a plurality of probes—for example, a probe used to introduce ionization gas to a lumen, and another probe comprising a discharge electrode which induces plasma in the ionization gas. More than one of either type of partial probe may be provided.

At block 112 (FIG. 1A), in some embodiments, plasma is generated. The plasma is optionally generated by a plasma generating module which is positioned at a distal end of a plasma probe, that is, the end of the plasma probe which is nearest to the targeted treatment region. Alternatively, in some embodiments, plasma is generated proximal to the site of delivery (e.g., by equipment located external to the body), and delivered along a conduit. The plume may be directed outward from the probe in any direction (e.g., laterally, distally along a longitudinal axis of the probe, or in another direction). There may be more than one plasma plume produced. However, even in such cases, there are generally limits on how large an area can be simultaneously contacted by plasma, particularly when working with small-diameter probes. Accordingly, there is, in some embodiments, a need to not only reach a target with a probe and generate plasma, but also to control distribution of that plasma so that it reaches all parts of a region targeted for treatment.

More particularly, the dose of plasma each portion of the targeted treatment region receives may be understood as roughly equivalent to the time integral of the rate at which reactive plasma species reach the target. Accordingly, at block 114, in some embodiments of the present disclosure, the probe is automatically moved, not only to cover the intended target, but also to direct plasma to the targeted treatment region with motions timed to appropriately regulate plasma dosing according to a predetermined target dosing.

The movement may be of any one or more of different types. For example, the motion may be through an open space or it may comprise motion by penetration (e.g., as by a needle or introducer) to within the volume of a tissue. Plasma may be delivered during motion (e.g., during motion through a scanning pattern to cover a whole target region), and/or plasma may be delivered from one or more static locations, from which said locations reactive species travel further to reach the remainder of the targeted region.

Automatic movement (compared to manual) has the particular potential advantage of allowing providing (and optionally tracking) a selected amount of plasma—e.g., enough to yield expected treatment effects, without overexposing tissue. Problems of overexposure to plasma can arise, for example, by heating effects. However, overexposure problems may also arise inasmuch as some proposed effects of plasma treatment are “differential” in nature—for while diseased tissue and/or pathogens may be particularly vulnerable to the plasma energy or reactive species in plasma, even normal tissue may have some vulnerability to it. A treated region, too, may be subject to undesired effects upon overexposure to plasma. Using an automatic positioning system helps to ensure that the amount of plasma actually delivered remains within dosing limits that have been set.

When the rate of plasma production is sufficiently constant, motion is under sufficiently tight control (e.g., predictable motion for a particular controller input), and the target position is sufficiently stable and well-known, it may be possible to automatically perform the method of FIG. 1A in an open-loop configuration, by moving the probe without feedback controls on its motion. However, in this case there is a potential for variation in the rate of plasma delivery, and/or for mismatches to occur between commanded movements, and movements which actually occur.

The operations at each of blocks 122 and 132 (FIGS. 1B, 1C) may be understood to encompass operations of blocks 112 and 114 (to generate plasma and move appropriately to deliver a selected plasma dose), but with the addition of further operations to help regulate that that motion and/or generation, based on what actually happens as a plasma treatment plan is carried out. The methods of FIGS. 1B and 1C are described separately, but they may occur together.

In FIG. 1B, at block 124, a current rate of plasma delivery is measured and/or estimated, and at block 126, motion is adjusted according to the current rate of plasma delivery. Conversely, in FIG. 1C, at block 134, actual motion is measured and/or estimated, and at block 136 the rate of plasma delivery is adjusted according to the estimated actual motion. Termination conditions for the loops of FIGS. 1B-1C are tested at blocks 128, 138. If not finished, the loops continue until they are finished, and then the flowcharts end.

For use in estimating a current rate of plasma delivery (block 124), one or more types of measurement are performed. In some embodiments, the measurement comprises monitoring actual power dissipated in the production of plasma. In some embodiments, the measurement comprises making spectral measurements of plasma generated. This can give data not only on how much plasma overall is being generated (e.g., on the basis of overall intensity), but also (e.g., on the basis of relative spectral peak amplitudes) how much of a given reactive species is being generated. This can be useful when a therapeutic reactive species is generated secondarily, e.g., OH reactive species, generated from water when exposed to plasma ions. For the same plasma power generated, there may be more or less of such secondarily generated species generated, depending, e.g., on how much of the ionizing source material is present at the site of delivery. In some embodiments, temperature is used as a proxy for plasma delivery, particularly if temperature change itself is among the treatment effects intended.

When changes are observed, one adjustment, performed in some embodiments, is to attempt adjusting the rate of plasma generation itself. However, this may not always be a viable or sufficient option. For example, there may not be enough water at the site to generate OH at the targeted rate, or there may be a partial impairment of plasma generation, e.g., due to contamination, lack of sufficient working space (distance to develop a full-powered plasma plume), a limitation on ionization gas flow, or another reason.

Accordingly, in some embodiments, compensation for changes from a targeted plasma rate comprise changes in motion. This may comprise reduction in a rate of motion, and/or in an elongation of dwell times at one or more positions of the plasma generating module.

As to the estimation of motion (block 134), there may be positioning error associated with a robotically controlled probe, e.g., particularly a flexible probe which may, under some circumstances, flex or strain, rather than fully faithfully replicate commanded motions. Again, motion itself may be adjusted in compensation. The motion adjustment itself may actually directly produce a change rate of plasma delivery (e.g., plasma generation), since, e.g., allowing more room for a plasma plume to play can in turn result in a higher power delivery into the plasma plume. Additionally or alternatively, another parameter affecting plasma delivery is adjusted, for example, a rate of gas flow. Termination of plasma generation is another option used in some embodiments, for example, to avoid excess exposure to plasma during recovery or recalibration period while the probe is maneuvered back into position.

Systems for Controlling Plasma Dosage

Reference is now made to FIGS. 2A-2D, which schematically represent systems implementing control of plasma delivery via an intrabody plasma delivery probe 12, according to some embodiments of the present disclosure.

The control configuration shown in FIGS. 2A-2D indicate different control configurations, providing different implementations of the general functionalities of plasma dose control, plasma probe control, probe sensing, and/or plasma dosimetry. Furthermore, the functions indicated may be implemented with different specific features, for example as next listed:

- Sensing of plasma probe 12 and/or delivery state of plasma: In some embodiments, sensing is performed for one or more of temperature (of plasma, tissue, and/or system components such as the probe), power, current, voltage, flow (of ionization gas or another fluid), pressure, impedance (of plasma, tissue and/or system components), and/or mechanical force. Chemical composition of plasma may be measured, for example, by its spectral emissions. Additionally or alternatively, spectral emissions from target areas interacting with plasma may provide signatures indicative of chemical composition of the target area. In some embodiments, sensor data is conveyed from the probe 12 using one or more sensor lines 32, which may be physical wires, for example. Optionally, wireless (radio) communication is used to communicate sensor data. The sensor 32A itself is shown near the tip of probe 12, but may be be in any suitable position according to its sensing modality, for example, inside the probe 12 (e.g., on an inner wall of probe 12 or floating inside a lumen of probe 12), and/or outside of probe 12 (e.g., on an outer wall of probe 12, or floating on a connector that outside or probe 12). A portion of sensor 32A may be located away from probe 12; for example, sensor 32A may comprise a fiber optic detector on probe 12, with spectral sensing itself performed by a module located proximally (e.g., located with control unit 10, controller unit 42 and/or positioning system 11) 42 and/or positioning system 11). Examples of sensor 32A modalities include sensing of temperature (e.g., temperature of and/or near the plasma plume), and collection and analysis of spectral emissions from plasma. In some embodiments, sensing of dissipated power is performed remotely from the probe, e.g, by monitoring performance of the plasma control unit 10. In some embodiments, sensor 32A comprises a contact sensor (e.g., it is placed to detect contact of a distal end of probe 12 with a target surface). In some embodiments, sensor 32A comprises a distance sensor, for example, an ultrasound sensor or an electrode that can sense impedance changes due to the proximity of a tissue 20) wall. In some embodiments, sensor 32A comprises a position sensor, for example, a sensor that detects relative movement of the probe such as bending, or a distance of advance of the probe relative to a sheath or other reference location.

Plasma dose control: This comprises control of device parameters including one or more of power (e.g., via power conduit 34), flow of ionization gas or another fluid (e.g., via gas conduit 33), frequency, and/or duty cycle of the plasma delivery device. Control is optionally performed in a feedback mode, wherein control inputs are analyzed (e.g., any of the inputs just described in relation to sensing), and device parameters adjusted according to the state indicated by the control inputs. For example, if temperature is too high, duty cycle and/or power may be reduced. Adjusting frequency of power delivery also can have an effect on effective amount of delivered power. An increase in ionization gas flow may correspondingly decrease temperature.

Plasma probe control: This comprises control of probe size and/or shape; control of plasma plume 8 size, shape, and/or direction, controlled via one or more actuation lines 31. These parameters are optionally performed in a feedback mode based on control inputs.

Plasma dosimetry: sensed indications of plasma delivery and/or controlled levels of plasma output are used to estimate plasma dosimetry-how much plasma is delivered, to where, and/or with which properties.

Any of the systems of FIGS. 2A-2D may be provided with movement degrees of freedom under the control of a robotic positioning system 11; for example probe rotation 21, translation advance/retraction along axis 22A, side-to-side translation in one or two axes 22, and/or probe bending around one or two rotational axes 23.

Figure 2A:
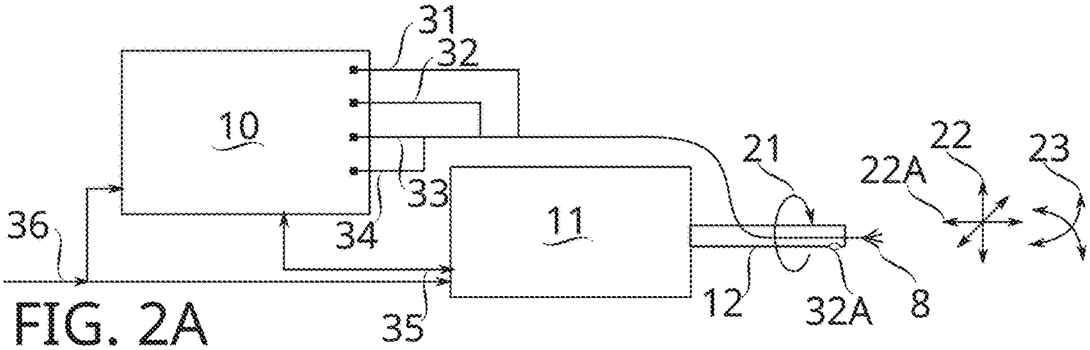
FIGS. 2A-2D schematically represent systems implementing control of plasma delivery via an intrabody plasma delivery probe, according to some embodiments of the present disclosure.

FIG. 2A represents preset controlled (open loop) systems, operating without the use of feedback loop configurations.

Ionization gas is provided through gas conduit 33, and electrical power to ionize provided gas to plasma is provided through power conduit 34.

Input line 36 represents a preset input. This may be provided as one or more system setting definitions, optionally used serially to configure and operate the system.

System setting definitions include:

Parameters to control the delivery of a pre-set plasma dosage.

Positions prescribed for the delivery of the plasma dosage.

Configuration of the probe 12 which delivers the plasma dosage.

Parameters of system setting definitions provided as the preset input may be determined in part based on diagnostic information derived from any suitable modality, for example, visual, ultrasound, X-ray, MRI and/or CT imaging. The imaging may be used, for example, to determine the shape and location of a treatment target. From this information, a positioning plan may be designed—for example, a plan which places a plasma delivery probe 12 at a plurality of different locations within and/or nearby the treatment target, with the object of obtaining complete plasma coverage. Plasma dosage at each position may be adjusted, for example to accommodate the shape of the zone which is to be treated from the position. Parameters of plasma generation itself may be selected according to knowledge of the target type.

Optionally, sensing (the signals of which are transmitted, for example, via sensor line 32) is used to confirm device operation. The preset is optionally adjusted (manually) if it is found that the device and/or its operating conditions are not as anticipated. Although in open loop mode the sensing is not used to automatically tune operational settings, sensing may be used to control automatic start/stop of probe operation; for example stopping device operation if safety limits (e.g., thermal limits) are exceeded, and restarting when those limits are restored. Temperature indications may be used as a basis for manually adjusting a global balance between rate of plasma generation and rate of probe movement; for example, a probe running too hot may be moved more quickly, and switched to a pattern of movement that returns to under-exposed areas in one or more subsequent passes.

The preset inputs 36 are sent to any of the sub-systems. Triggers and control/sensing signals are exchanged (via one or more signal lines 35) between the positioning system 11 and the plasma control unit 10 to synchronize operation.

Plasma delivery probe 12 is assembled on the positioning system and the positioning system is responsible for the positioning and movement of the probe.

Figure 2B:
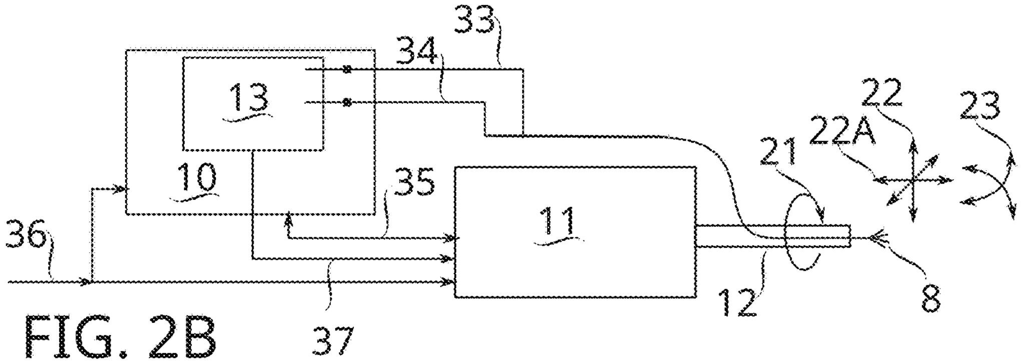

FIG. 2B illustrates a configuration of a feedback controlled (closed loop) system, wherein dosimetry monitoring is used as input to the determination of plasma generating parameters. In this configuration, dosimetry uses measurements of what is provided on the side of the plasma control unit (e.g., in contrast with measurements of the generated plasma itself). Furthermore, control is primarily maintained by the positioning system 11, which integrates feedback to determine how its own positioning should be adjusted, and/or issues instructions back to the plasma control unit 10 based on feedback it receives.

Plasma control unit 10 includes dosimetry module 13, which monitors and controls the delivery of ionization gas and energy through lines 33, 34. Dosimetry module 13 provides dosimetry information (as measured and/or as controlled) the positioning system 11 via dosimetry signal line 37. This gives feedback which may be used to adjust probe positioning: for example, distance from target, and/or rate of scanning movements which direct plasma across different regions of the target.

As also described for FIG. 2A, a preset input 36 may be provided which is sent to any of the sub-systems. Triggers and control/sensing signals are exchanged on signal line(s) 35 between the positioning system 11 and the plasma control unit 10 to synchronize operation. Synchronization targets may also be adjusted based on the feedback which positioning system 11 receives.

Probe 12 is coupled to the positioning system 11, and the positioning system is responsible for the positioning and movement of the probe. The actuation devices and mechanical linkages which couple probe 12 to positioning system 11 may be of any type known in the art. For example, stepper motors and/or server motors may be used move mechanical linkages. The mechanical linkages may be implemented, for example, using known mechanisms such as lead screws, levers, and/or control wires. Insofar as it controls positioning, positioning system 11 also controls the delivery of prescribed plasma dosage through the timing and/or patterning of the motions of probe 12.

Figure 2C:
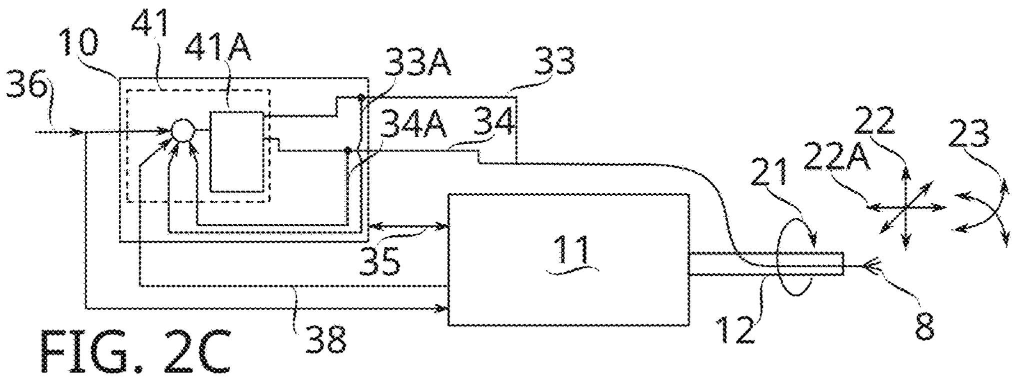

FIG. 2C illustrates another feedback controlled (closed loop) system configuration, with dosimetry and plasma parameter signals provided as feedback for automatically adjusting dose control by plasma control unit 10. As in FIG. 2B, dosimetry is based on measurements on the controller side. But FIG. 1C emphasizes feedback-modulated dose control occurring within the plasma control unit 0 itself.

Target dosing is indicated to dose control unit 41 by inputs 36. Dose control unit 41 receives inputs 34A, 33A respectively indicative of energy and ionization gas provided to the probe 12. It may also receive position feedback 38 from positioning system 10.

In some embodiments, feedback from positioning system 10 is provided in the form of position data indicating the position of probe 12. Dose control unit 41 processes the data to control the power levels to achieve targeted dosage.

Additionally or alternatively, positioning system 10 directly provides indications of targeted dosage (e.g., varying for different positions and/or rates of probe scanning over the target area), and dose control unit issues instructions to controller module 41A which acts as gas controller and energy controller to direct the generation of plasma according to these indications of targeted dosage.

The control methods of FIGS. 1B and 1C are not mutually exclusive. For example, in some embodiments, control is coordinated bidirectionally, such that movements produced by positioning system 10 are adjusted to accommodate in part the present dosage strength (power level and ionization gas flow rate, for example), while the present dosage strength instructed by does control unit 10 is in turn adjusted to accommodate in part variation in movement produced by positioning system 10. Which is adjusted when (and how much) may be determined, for 20) example, based on which system is working closest to its operating limits, and/or to correct with one of the two control subsystems a discrepancy between instructed and measured movements or dosage strength which occur in the functioning of the other. In some embodiments, the bidirectional control is coordinated by a master controller which selects which subsystem to adjust based on received feedback. In some embodiment, the bidirectional control is implemented by a protocol established direct between the dose control unit 41 and the positioning system 11.

Figure 2D:
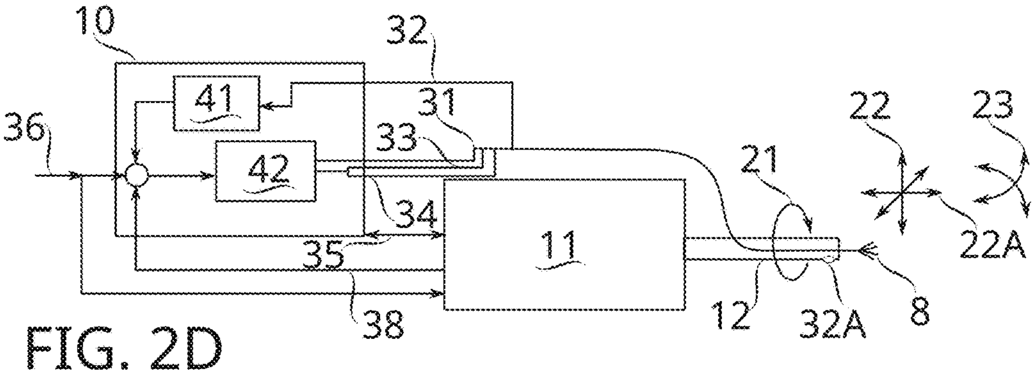

FIG. 2D illustrates another feedback controlled (closed loop) system configuration, in which feedback and control more directly involves probe 12 itself. In the configuration shown, plasma control unit 10 is provided with a connection via actuation line(s) 31 of the probe and/or probe tip. Actuation may relate to the dosage and/or characteristics of plasma being delivered. In some embodiments, probe actuation has effects on probe positioning which are not under the direct control of positioning system 11.

Probe sensing capabilities are also provided at the plasma applicator/tip/probe, and sensing data communicated via one or more sensor lines 32. Optionally only one of these two is provided. Actuation of the probe may be controlled based on feedback implemented as described in relation to FIGS. 1B-1C. Conversely, sensing from the probe may be used as feedback, used to determine settings for providing ionization gas and/or energy by plasma control unit 10, and/or to as feedback to help regulate motions commanded by positioning system 11.

In some embodiments, positioning system 11 provides dynamic positioning feedback to the plasma control unit 10 and a controller unit 42 thereof. Controller unit 42 controls operating parameters of the probe 12 itself (e.g., actuation of moving parts) to put it in a probe configuration which is suitable to achieve an intended dosage suitable for the movements being carried out. Additionally or alternatively, positioning system 11 itself determines how probe 12 should be actuated, and instructs controller unit 42 accordingly with direct instructions of how probe 12 should be actuated. In either case, control may be modulated based on feedback received over sensor line(s) 32, optionally after conditioning by sensor signal conditioner 41. Coordination between subsystems (e.g., when both are actively modified based on feedback) may be managed by a higher-level control system, and/or a communication protocol established between the positioning system 11 and the plasma control unit 10.

Movement and Positioning Patterns for Plasma Delivery

Reference is now made to FIGS. 3A-3D, which schematically represent different patterns of plasma delivery probe movements by which plasma may be delivered to within the volume of a tissue, according to some embodiments of the present disclosure. Each of the patterns shown is implemented using one or more penetrating elements 301, each of which may be, for example, a needle configured to emit a flow of plasma from one or more distal apertures.

Figure 3A:
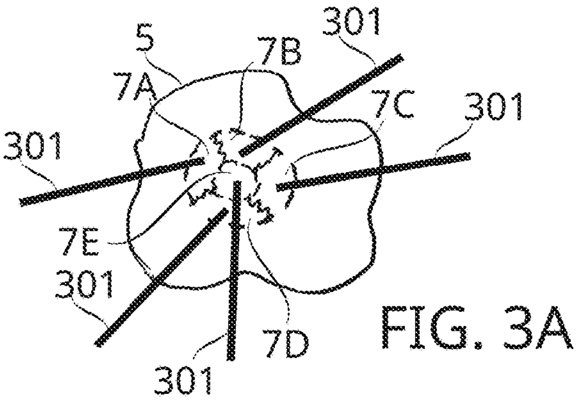
FIGS. 3A-3D schematically represent different patterns of plasma delivery probe movements by which plasma may be delivered directly from within the volume of a tissue, according to some embodiments of the present disclosure.

In FIG. 3A, a plasma control unit is controlled in conjunction with a probe positioning system to provide treatment to tissue across the full treatment site by sequential (or, optionally, at least partially simultaneously) access at multiple needle penetration locations. For example, each position of a needle 301 shown may be a different position of the same needle at different times, or a plurality of needles may be provided which penetrate the target at the same time. The target itself resides within the volume of a tissue 5, and comprises targeted segments 7A, 7B, 7C, 7D, and 7E. For treatment of each segment 7A-7E, a distal tip of needle 301 is inserted to its approximate center, and plasma delivered from one or more apertures thereof. The effects (reactive species and/or cascade effects) generated in and/or by the plasma diffuse through the corresponding segment 7A-7E. Optionally, plasma treatment is given at different depths of penetration along the same needle track, for example as described for the treatment pattern of FIG. 3D.

Figure 3B:
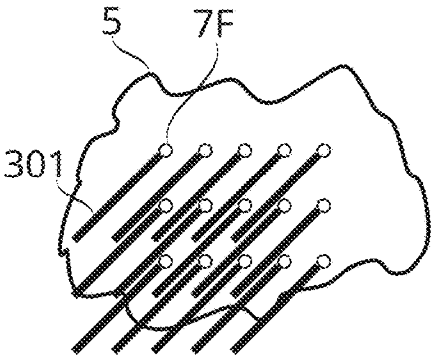

In FIG. 3B, a plasma control unit is controlled in conjunction with a probe positioning system to provide plasma treatment to tissue delivered at multiple target sites 7F arranged in a grid or grid-like fashion. For purposes of illustration, the probes 301 are shown approaching each from a same angle which happens to be oblique to a plane in which zones 7F are arranged. A perpendicular approach is alternatively performed in some embodiments of the present disclosure.

The pitch of the grid may be constant. Alternatively, the pitch of the grid may be varied, for example to accommodate the specific geometry of the target. A square grid is shown in FIG. 3B. Optionally, the sites of the grid are arranged in another manner, such as on a hexagonal grid spacing, radially (e.g., as concentric circles or spokes from a center), and/or concentrically (e.g., as nested loop loops following the target perimeter). Optionally, variation in the density of sites 7F is used to vary intensity of plasma dose delivery (e.g., closer densities are used where dose delivery is to be increased). Optionally variation in the density of sites 7F is used to allow reducing probe dwell time at any given point, which may provide a potential advantage for regulation of potential thermal effects of the treatment delivery.

Optionally, the target sites 7F are treated in a rastered order (e.g., row by row), or in another pattern (e.g., dithered, interlaced, or randomly ordered). As illustrated, the approach to each of the target sites 7F is from a same side of the volume of the tissue 5 in which the target sites 7F are embedded, which is particularly suited to the robotic movements of a single probe by successive penetrations, withdrawals, and translations to a next site for the next penetration. In some embodiments, raster patterns are used from a plurality of directions for example, similar to the zonal pattern of FIG. 3A, but with each individual needle position being replaced by a 2-D pattern of needle penetrations.

Again, reactive species generated in and/or by diffuse from the actual position of deliver to a larger surrounding region of tissue. Optionally, plasma treatment is given at different depths of penetration along the same needle track (discretely or continuously), for example as described for the treatment pattern of FIG. 3D—this would result in a 3-D pattern of plasma placement. Without tissue penetration, this configuration is optionally used to treat a surface area which is larger than the area which can be effectively reached by plasma treatments from a single probe position.

Figure 3C:
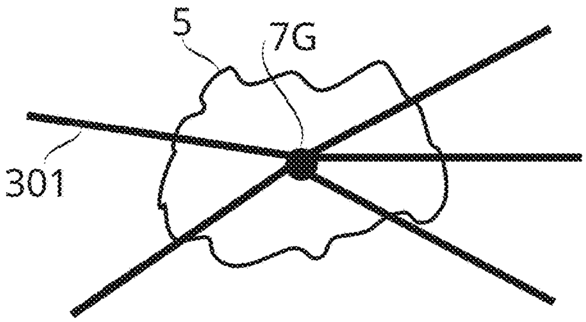

In FIG. 3C, a plasma control unit is controlled in conjunction with a probe positioning system to provide plasma treatment to a same tissue region 7G from a plurality of directions of insertion to tissue 5 of probe 301. Multiple penetrations to the same region are optionally coupled to penetrations reaching multiple different target sites, for example as described in relation to FIGS. 3A-3B. In some embodiments, different probes are used for different functions; for example, a first probe may deliver ionization gas, a second probe may scavenge it, and a third probe may comprise a discharge electrode which actually ionizes delivered ionization gas into plasma. In some embodiments, a probe is dedicated to delivering a non-ionization gas fluid, for example, saline, to produce effects of cooling and/or for generation of secondary reactive species upon interaction with plasma. In some embodiments, providing multiple simultaneous probes to a single region allows a higher peak rate of plasma generation and/or delivery.

Figure 3D:
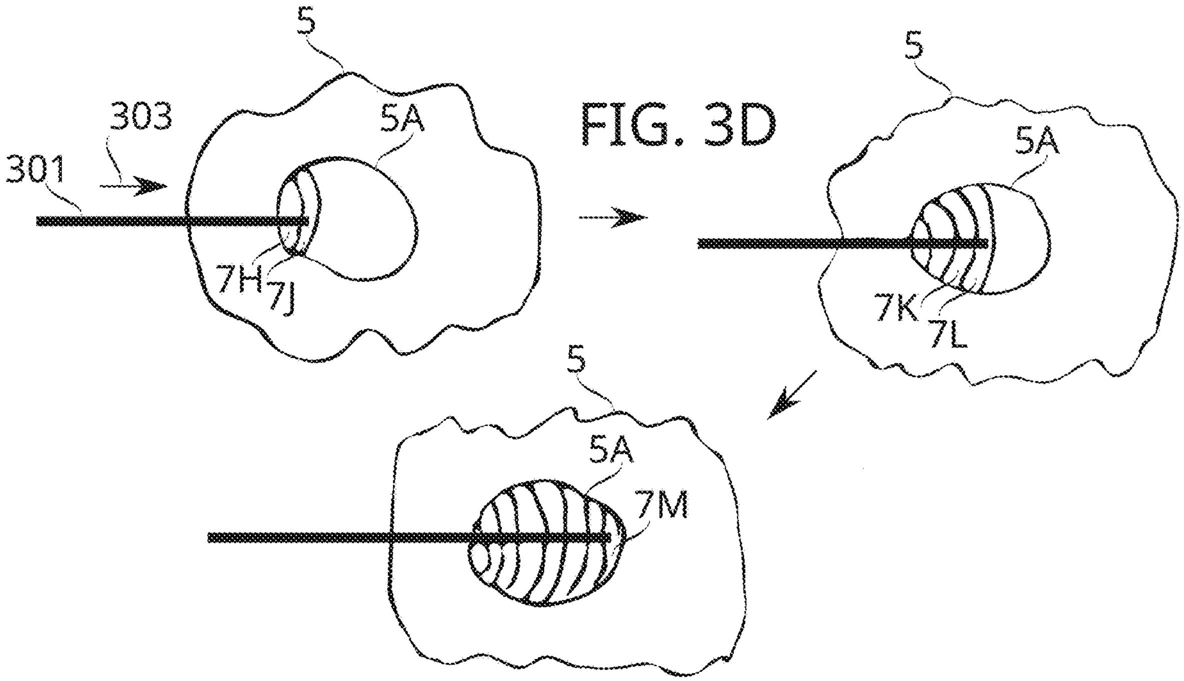

In FIG. 3D, a plasma control unit is controlled in conjunction with a probe positioning system to provide plasma treatment via probe 301 advancing along a track in direction 303 to discharge plasma into successive tissue regions 7H, 7J, 7K, 7L, 7M. Three panels are shown representing stages during a single needle penetration of a target area 5A within the volume of tissue 5. In the first panel of FIG. 3D, needle 310 is delivering plasma into tissue region 7J, after having also penetrated and delivered plasma within zone 7H. The second panel shows delivery of plasma into tissue region 7L, after having also delivered plasma within zone 7L. The third and final panel shows other tissue regions, including a final tissue region 7M into which plasma is directly delivered.

The tissue regions 7H-7M are shown as discreet bands representing bands of reactive species diffusion which may occur in a target with anisotropic diffusion properties (e.g., a laminar internal structure, and/or a crossing circulatory flow. In some embodiments, the zone which receives treatment from each successive position of needle 301 extends roughly spherically from the distal end of needle 301 (e.g., as illustrated and described in relation to FIG. 4A). In a "zonal" mode of plasma delivery, used in some embodiments, the needle is moved so that it pauses at each successive depth, and dwells there during plasma delivery until the dose is complete. The zonal mode of plasma delivery has potential advantages for simplifying and/or stabilizing dose delivery. Alternatively, in some embodiments, plasma probe movement is continuous during dose delivery, which has the potential advantages of reducing buildup of reactive species and/or temperature in any single location, and of smoothing out dose delivery. Plasma delivery may be during penetration (in direction 303) by probe 301, and/or during withdrawal (in a direction opposite to direction 303).

The operation of a plasma delivery probe may be subject to disruptions due to interactions with its environment that introduce significant variations in the effective treatment by plasma being delivered at any given moment.

For example, as ionization gas flows to the treatment site, it may periodically build up pressure that releases suddenly, e.g., to flow back along a needle track. These pressure swings may create pulsation (regular or irregular) of the effective instantaneous generation of plasma at the site. Active scavenging of gas (e.g., via the needle) is optionally performed in some embodiments, potentially reducing gas build up. But the scavenging lumen may itself be subject to partial clogging, e.g., by blood or simply upon passing through a relatively more constricted area of tissue. Electrical variation can also occur, e.g., as changing tissue conditions cause impedance changes affecting the generation of plasma. Accordingly, in some embodiments, feedback control is used to help ensure that the overall amount of plasma delivered to different target sites remains within a targeted range of plasma exposure.

Reference is now made to FIG. 4A, which schematically represents a plasma control unit controlled in conjunction with a probe positioning system to provide plasma treatment from within a lumen 401, according to some embodiments of the present disclosure. In some embodiments, the motion control comprises advancing and retracting probe 430 along a longitudinal axis of lumen 401, and/or rotating probe 430 around the longitudinal axis. As for the case of delivery of plasma directly into the volume of a tissue, rate of movement and/or dwell time can be controlled to manage plasma dose delivery. Optionally, this includes controlling the rate of movement and/or dwell time to compensate for instantaneous variations in plasma generation intensity, maintaining the targeted dosage.

Lumen 401 may be, for example, a blood vessel, an airway, a lumen of the digestive tract, or a lumen of the urinary tract. Where the lumen is an empty (gas-filled) or readily evacuated lumen (e.g., a digestive or urinary tract lumen), the plasma may be delivered into the lumen from a probe as it is continuously advanced into and/or retracted from the lumen. In a liquid-filled lumen (e.g., a vascular lumen normally filled with blood), it may be preferable to advance through the lumen in stages, sealing off a portion of the lumen at each stage of advance (e.g., using balloon anchors, for example, as described in relation to FIGS. 4B-4C). However either site is compatible with either pattern of delivery, e.g., by pausing during the advance/retraction to deliver plasma (in the case of the emptied lumens), or by sliding anchors while they remain deployed in a scaling position in the case of delivery plasma into a normally liquid-filled lumen. Plasma is delivered, for example, in a distal-pointing direction, in a side pointing direction, or in an obliquely pointing direction. Together with side- and oblique-pointing plasma plumes, rotation of the probe is optionally performed to spread the dose around a circumferential (e.g., ring-shaped) portion of the target tissue.

Illustrated particularly in FIG. 4A are four discrete sites of plasma delivery 410, 412, 414, 416, accessed sequentially by advance of a distal end of probe 430 longitudinally along lumen 401. The thick dotted line portion of probe 430 represents positions of longitudinal advance beyond a position with a distal end of probe 430 at location 410.

The sets of concentric rings 410A, 412A, 414A, 416A represent diffusion of reactive plasma species, plasma energy, and/or effects cascading from plasma exposure into surrounding tissue 5, to increasingly lowered concentrations. Some tissue regions (e.g., near to a particular site of plasma delivery 410, 412, 414, 416) may receive plasma mainly from one or two sites. Other treatment target sites (e.g., about half way between sites 412, 414) may receive reactive species diffusing respectively from a plurality of different sites of original plasma delivery.

Reference is now made to FIGS. 4B-4C, which schematically represent a plasma delivery probe 430 equipped with a deployable docking mechanism 431, and configured to deliver plasma from plasma generating module 440 in one or both of a direction lateral to a longitudinal axis of the probe 430 (FIG. 4B), and a direction along the longitudinal axis of the probe 430 (FIG. 4C).

In some embodiments, deployable docking mechanism 431 is a stabilizing mechanism, which helps to maintain a selected spacing between the site of plasma generation on plasma generating module 440, and treatment target sites along lumen 401. The spacing may be a minimal spacing, selected, for example, to prevent blockage of ionization gas flow and/or to ensure that plasma plume length will be optimal to deliver the targeted rate of plasma dosing. In some embodiments, engagement of docking mechanism 431 with the wall of lumen 401 is sufficient loose as to allow rotatingly sliding and/or longitudinally sliding docking mechanism 431 within lumen 401 while deployed. Rotating may be achieved, for example, by twisting the main body of probe 430 itself (e.g., by use of an actuator of a robotic controller), and/or by rotating plasma generating module 440 relative to probe 430, e.g., rotating it about a bearing under the force of escaping ionization gas, or another actuating mechanism.

In the embodiment shown, docking mechanism 431 maintains spacing for plasma emitted from a lateral side of plasma generating module 440. In some embodiments, spacing is ensured on a distal side of plasma generating module by a balloon or other atraumatic device; additionally or alternatively, sufficient distal-side spacing is ensured simply by placing the discharge electrode(s) of plasma generating module 440 sufficiently proximal to allow distal space for plasma plume development.

The docking mechanism 431, in some embodiments, is used for variable centering of plasma generating module 440, for example, under robotic control.

In some embodiments, control of a deployment state of docking mechanism 431 in turn controls spacing of probe 431 from the circumferential wall of lumen 401. Again, this provides a potential advantage for control of the length of plasma plume 435 and/or the impedance environment of plasma generation, and, correspondingly, a rate of plasma dosage delivery.

In some embodiments, docking mechanism 431 comprise one or more spacers 433A, 433B. Optionally, these deploy to a relatively fixed size (e.g., are inflated to a relatively high pressure), and act as a "ruler" setting a minimum plasma plume length (wall-to-probe distance). Spacer 434, in some embodiments, deploys to press spacers 433A, 433B against the tissue wall. Optionally, it remains compliant compared to the relative stiffness of deployed spacers 433A, 433B to help maintain their intended spacing distance, either by preventing any collapse, or by limiting collapse to, for example, less than 33% of the fully deployed radial length of deployed spacers 433A, 433B. In this way, the length of plasma plume 435 can be maintained within a targeted functional range of lengths.

In some embodiments (FIG. 4C), docking mechanism spacers 433A, 433B, 434 can be deployed to various extents and/or pressurizations to control the relative centering of a longitudinally directed plasma plume 436, e.g., to play against a target surface area (e.g., of a tumor or blockage 437) distal to plasma probe 430. Rotating the plasma probe 430 (e.g., under robotic control) can generate a roughly circular treatment region, while changing centering of plasma probe 430 adjust the radius of this treatment region.

In some embodiments, spacers 433A, 433B (optionally together with spacer 434) are actuatable to create a fully sealed space when expanded, for example, the space occupied by plasma plume 435 in FIG. 4B. In some embodiments, this space is evacuated (e.g., by suction and replacement with ionization gas) through one or more apertures of plasma probe 430. This allows plasma delivery against tissue surfaces which are normally in a liquid fluid environment. Scaling mechanisms of this type are described, for example, in International Patent Application No. IL2021/050303 entitled "Treatment of Internal Spaces Using Plasma Generating Device", filed Mar. 18, 2021; the contents of which are included by reference herein in their entirety.

The sealed space is optional. In some embodiments, a docking mechanism 431 comprises a different configuration of spacing elements, for example, a toroidal balloon, a pair of oppositely positioned balloons, three or more circumferentially spaced balloons, or one or more deployable solid spacers. Examples of solid spacers include elastic metal wires, preferably atraumatically tipped, for example, with a soft polymer. Another example of a solid spacer is a shaped (e.g., lamellar) polymer element can be deployed and/or deformed to project radially away from the central body of plasma generating module 440.

The spacing elements may be symmetrical or asymmetrical to generate spacing. For example, a toroidal balloon may be asymmetric and/or asymmetrically distendable to allow eccentric positioning of plasma generating module. Separate balloons are optionally inflated to different pressures to help control probe centering, and/or the balloons are constructed differently to expand to different extents and/or with different elastic compliances. Deployable wire spacers may be provided with different relative elasticities, e.g., so that one sets a minimal distance to a wall, and one assists to press the probe up to that minimal distance. Additionally or alternatively, deployable wire spacers can be advanced to different degrees to control the centering position of the plasma generating probe 440.

It is again noted that the center-spacing of a plasma generating probe can be used as a way of controlling plasma dose delivery, insofar as it can be used to control plasma plume length. In particular, monitoring data which indicate lower than targeted power delivery can be used as a basis for adjusting the center spacing of a plasma generating probe, e.g., adjusting tension in one or more of spacers 433A, 433B and/or 434 (or another spacing element).

Conversely, imprecision and/or errors in positioning relative to the target wall (whether detected directly by measurement of distance, or indirectly, e.g., by monitoring of plasma power delivery) is optionally compensated for by adjusting parameters of plasma generation (e.g., ionization gas rate of flow), and/or parameters of plasma movement, e.g., as executing under robotic control.

Plasma can be delivered in bursts or continuously; at static locations (one or a plurality of them) or in locations which change smoothly as a probe is rotated, inserted, or retracted. For example, in some embodiments, an area targeted for treatment comprises a longitudinally extended region concentrated on one side of a longitudinally extended lumen. Optionally, the pattern of plasma generating module movement for treating this area is corkscrew shaped (comprising simultaneous rotation and longitudinal advance). While the probe moves along this path, generation of plasma is turned off and on intermittently as the plasma plume generation site is periodically oriented away from or toward the target area. Continuous rotational movement in a single direction has the potential advantage of reducing hysteresis (e.g., due to probe twisting and untwisting) which can arise from a raster scanning pattern which periodically reverses direction.

Reference is now made to FIGS. 4D-4F, which schematically represent positioning of plasma generating module 440 within a branched lumenal structure 402, according to some embodiments of the present disclosure. The branched lumenal structure 402 comprises, for example, a portion of a lung or vasculature. Plasma generating module 440 is illustrated equipped with an optional docking mechanism 431, which may be configured, for example, as described in relation to FIG. 4B-4C (e.g., allowing control of centering). In some embodiments, the docking mechanism is omitted. Steering into different branches 402A, 402B, 402C of branched lumenal structure 402 is optionally performed using a guide wire. In some embodiments, probe 430 is itself steerable, e.g., using one or more distally-attached wires which can be tensioned in order to pull some portion of probe 430 into a curved shape.

In some embodiments, a plurality of positions (e.g., two or more of those shown in FIGS. 4D-4F) are optionally assumed simultaneously by different plasma generating modules 440. They may be inserted in parallel and steered to different branches, and/or they may be located at different longitudinal positions along a single probe, each receiving its own portion of electrical current and ionization gas, e.g., from a common power cable and common gas feed lumen.

Figure 5A:
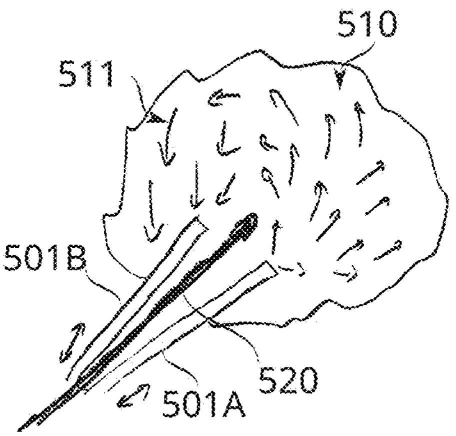
FIGS. 5A-5B schematically represent manipulation of ionization gas flow field patterns to control plasma dosing, according to some embodiments of the present disclosure.
Figure 5B:
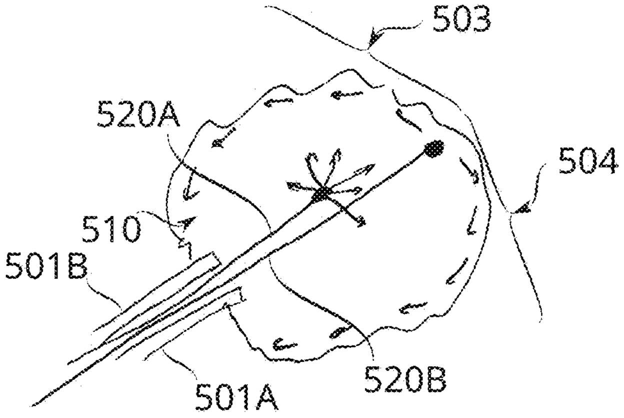

Reference is now made to FIGS. 5A-5B, which schematically represent manipulation of ionization gas flow field patterns to control plasma dosing, according to some embodiments of the present disclosure.

In some embodiments, targeted tissue is treated via plasma interactions with the lumenal surface of a large gas-filled lumen. In some embodiments, dosage is partially controlled by knowledge and/or manipulation of patterns of ionization gas flow. Ionization gas flow rate is optionally selected from within a range of about 0.1 L/min to about 10 L/min. Optionally, duty cycle of plasma generation is adjusted, for example, within a range of about 10% to 100%.

In FIG. 5A, two gas lumens 501A, 501B have been introduced to lumenal space 510, and used to introduce ionization gas into lumenal spaced 510. Gas flow is shown flowing in a pattern 511 generally from gas lumen 501A to 501B, but the direction of gas flow is optionally reversed at any time. Since the whole lumen is suffused with ionization gas, discharge electrode 520 can be operated at any point within it. While flow is maintained, dosing achieved will be dependent not 20) only on the position of discharge electrode 520, but also on the direction of the gas flow field surrounding it.

In FIG. 5B, two different positions of (optionally the same, but at different times) discharge electrode 520 are shown as discharge electrode 520A and discharge electrode 520B. Discharge electrode 520A is operated near the center of lumen 510, while discharge electrode 520B is operated near the lumenal wall.

The field of gas flow is similarly divided into different times, with different flow fields. Flow indicating arrows 503 on the upper/left side of an axis extending generally along electrode 520B (lumenal wall) or electrode 520A (lumenal center) correspond to portions of a flow field 511, with flow being generally counterclockwise. Flow indicating arrows 503 (remaining arrows) correspond to portions of a generally clockwise flow field, generated with the inlet and outlet roles of lumens 501B, 501A reversed from what is shown in FIG. 5A. The reversal allows different areas to be treated from the same electrode positions, under different flow regimes.

It may be noted in particular that the local direction of gas flow is constrained by the proximity of a wall to flow roughly parallel to the wall, with a direction influenced by the global pattern of flow.

With relatively low-energy introduction of gas, velocities of flow are affected by the proximity of one or both of the ionization gas inlet/outlet tubes 501A, 501B. In a non-vortex (and preferably laminar) flow: to the extent that one of them is close to an electrode, relatively more of the volumetric flow of gas is constrained to pass near the electrode, leading to a more rapid local flow velocity. If neither is close, then flow velocity may decrease. Depending, e.g., on the velocity at which gas is introduced, regions far from either lumen may be relatively stagnant, although inducing a turbulent flow (e.g., by using a higher flow velocity) may assist in spreading plasma more evenly throughout a lumenal space.

In some embodiments, a typical rate of gas introduction is energetic enough that for a reasonable-sized body lumen, a large portion of the gas in the lumen is induced into a laminar flow; optionally vortical and/or streaming between an inlet and an outlet. Movement of the probe perpendicular to the direction of streaming may be used to treat a stripe of the lumenal surface.

When the target is the whole of an interior lumenal surface (e.g., as part of a plasma treatment for a microbial infection), the generation of a strong flow field (e.g., enough to generate turbulence) may assist in helping to assure that all parts of the wall are covered.

In another example, a discharge electrode 520 may be left at a certain location (e.g., near a 20) focal target of plasma treatment), while the flow field is altered to flow in different directions. For example, flow may be generated sequentially in four directions with each vortex being oriented perpendicular or opposite to the others. In another example, gas flow may be directed so that a "pole" of a vortical flow (region near the axis of a vortex) occurs near the discharge electrode 520, so that plasma it creates is swirled within a relatively localized area.

In some embodiments, lumens 501A, 501B are dynamically positioned to shape the flow field. Decisions on placement of these lumens may be made based on prior knowledge of the shape of a lumen defined by the tissue. Sufficient predictability of dosing results is potentially achieved by bringing one or both of lumens 501A, 501B closer to electrode 520, and/or by placing and orienting them so that they create a vortex with a well-defined direction and/or central axis. Optionally, one or both of lumens 501A, 501B are articulated to allow their navigation to a wide range of positions and orientations within lumen 510 after introduction through a small entrance aperture. Discharge electrode 520 is positionable within the flow field so that it generates plasma that covers a target region as desired.

In some embodiments, flow field modelling known in the art is used to predict (e.g., based on knowledge of the lumen geometry) flow velocities at different lumenal positions under different conditions of gas introduction and withdrawal, and this model used as part of the calculations of dosage being received by any given portion of the lumenal wall.

Reference is now made to FIG. 6A-6G, which schematically represent different scanning patterns which may be used to move a plasma plume over a surface comprising a plasma treatment target, according to some embodiments of the present disclosure.

Figure 6A:
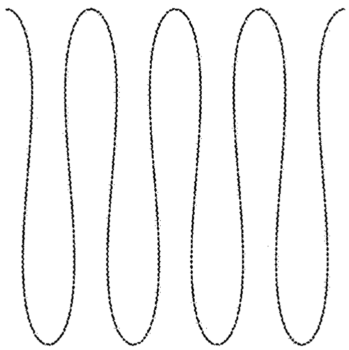
FIG. 6A-6G schematically represent different scanning patterns which may be used to move a plasma plume over a surface comprising a plasma treatment target, according to some embodiments of the present disclosure.
Figure 6B:
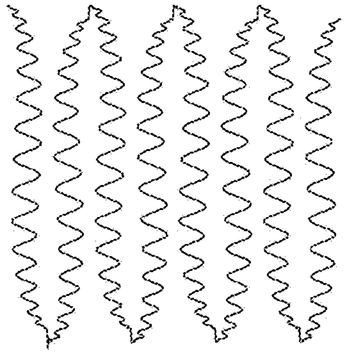
Figure 6C:
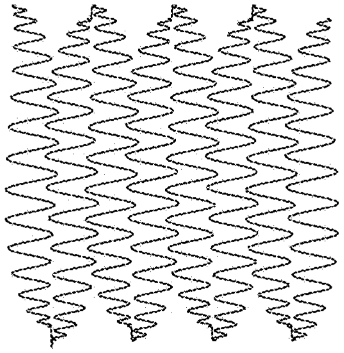

FIG. 6A shows a continuous back-and-forth scanning pattern. The pattern shown slightly "fattens" the path near the turns, which (compared to straight tracks) potentially reduces recent-time self-overlap of the plasma track (mitigating thermal buildup at the turns), while also slightly increasing the minimum radius of curvature being navigated. The "smoothing" provided by the latter provides a potential advantage for reducing high spatial and/or temporal frequency control requirements on a robotic actuation mechanism. FIGS. 6B and 6C superimpose modulation (e.g., approximately sinusoidal, as shown, or another "zig-zag" pattern) onto the overall back-and-forth scanning motion. This has the potential advantages of keeping any plasma plume "hot spot" in constant motion; and at the edges of the plasma plume, evening out the seam between adjacent long passes. In these figures and in others showing sinusoidal oscillations, it should be understood that there is no limitation to the particular oscillation shape shown. The secondary motions may be larger or smaller in amplitude, and they may be larger or smaller in spacing (oscillations per unit of net advance). The oscillation shape may alternatively be sinusoidal, triangular, square, sawtooth, or another shape. The oscillation need not be continuously advancing, either. For example, the pattern of movement may comprise looping motions, with each complete loop slightly offset along a general direction of overall track movement.

Figure 6D:
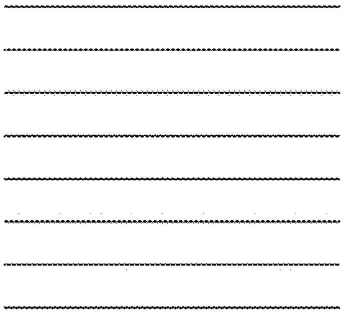
Figure 6E:
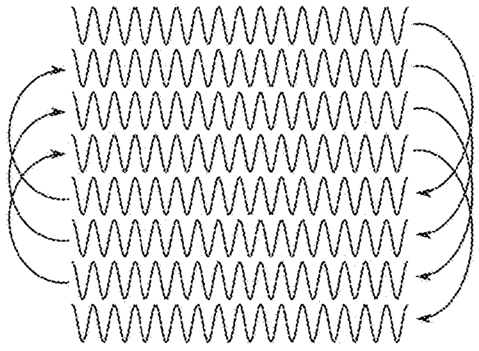

FIGS. 6D and 6E show interrupted patterns, wherein the plasma plume is optionally turned off (or simply moved without regard to dosing characteristics) between passes. In FIG. 6D, the patterns comprises straight-track passes, which can be performed in adjacent order or another (e.g., spaced from the previous pass) order. Directionality can be back-and-forth or unidirectional. FIG. 6E illustrates a pattern based on an interrupted straight track pattern like that of FIG. 6D, with a sinusoidal motion (representing superimposed high-frequencies motions more generally) added along each straight track, with potential advantages as described for FIGS. 6B-6C. The curved arrows show an example of a non-sequential pattern of tracks, which always keeps an interval of a third track's pass between passes along any two other adjacent tracks. A potential advantage of this is to mitigate a potential for thermal buildup.

Figure 6F:
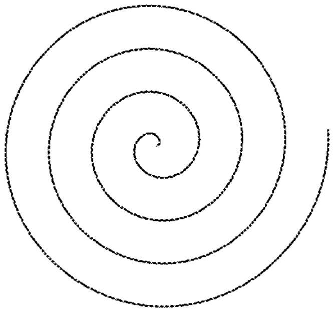
Figure 6G:
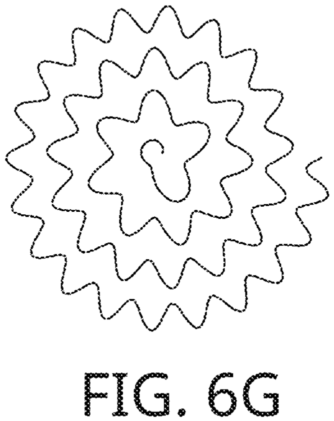

FIGS. 6F-6G show examples of spiral tracks, potentially well suited for (but not limited to) robotic actuation which operates via direct control of rotation and device centering. FIG. 6G again superimposes a sinusoidal pattern to the overall movement pattern, this time on the plain spiral of FIG. 6F. In some embodiments, a plurality of interlacing spiral tracks are followed. The pitch of the spiral tracks is optionally increased to maintain a large enough separation between coils of the spiral to avoid adverse cumulative heating effects. After tracing over a first spiral track, a second spiral track can be traced over through a region which is half-way between adjacent coils of the first spiral track.

Scanning patterns are implemented by any robotic controller which is configured to guide a plasma generating site (e.g., of a plasma generating module) through a controlled 2-axis pattern of movements matching the pattern. A third axis of movement is optionally added, for example, to accommodate tissue surface curvatures and/or irregularities (this is discussed more particularly in relation to FIG. 8, herein).

In some embodiments plasma is delivered from a stiff needle which is controlled by an actuator coupled to its a proximal end.

In some embodiments, the needle's proximal end itself moves in the same pattern of translation movements as the 2-D patterns shown that represent movement of its distal end. In some embodiments, the needle is swiveled (its angle is changed) as it moves (or to move it at all). This potentially adds a 3-D curvature to paths represented in two dimension by the drawings, but where desirable, a depth translation axis can be used to compensate. It is noted that body lumens themselves comprised curved walls, so pattern curvature induced by a "swinging" type control mechanism may provide a potential advantage for controlling probe-to-target distance.

Actuation comprising either or both of these types of motion is potentially compatible with any of the patterns shown in FIGS. 6A-6G, although control logic needed to coordinate axis movement may be simpler or more complex depending on how the control axes coordinates map onto tracks of the movement pattern. The parallel (or roughly parallel) track embodiments are particularly well suited to a robotic controller which performs motions primarily in a Cartesian coordinate system (e.g., as by an X-Y translation stage). Swivel-type control is well suited to a circular or spiral pattern. There may also be 3-D motions (adding depth) which translate the probe toward or away from the target, e.g., to accommodate depth of the target surface.

A robotic actuator with longitudinal and rotational positioning controls, e.g., as described in relation to FIG. 4B-4C, can also apply any of the illustrated plume movement patterns (against a curved surface) when the plasma plume is directed laterally. For example longitudinal advance and retraction, in some embodiments, guides each of a series of substantially parallel tracks, while rotational angle switches between tracks, and optionally oscillates, e.g., as described in relation to FIGS. 6B-6C and 6E. Conversely, tracks may be selected (and oscillation optionally implemented) by longitudinal movements, while rotation draws the plume along the main axis of each track.

In some embodiments, robot control moves the probe in a pattern comprising circumferential motion, for example a spiral, or a set of concentric circles. While this motion can also be produced by actuation of a stiff probe, it is also suitable for use with embodiments such as those described in relation to FIGS. 4B-4C which can be rotated (producing the circumferential motion), and also controlled (e.g., via actuation, such as by inflation, of a docking member) with respect to their centering (producing radial motion). Although the polar coordinate system established by a positioning system directly controlling radial distance and angular position is a natural fit for spiral and circular patterns, such a system is also potentially capable of moving the plasma plume in generally straight lines, using appropriately coupled variation of centering control (radius) and device rotation.

It is noted that a long flexible member (via which rotational position is controlled) is potentially susceptible to a twist hysteresis which affects responsiveness to changes in rotational direction. In some embodiments, this can be mitigated by maintaining rotation in a same direction all the time, and if necessary shutting off the plasma plume whenever its current position would cause it to play against an area outside the surface targeted for treatment.

A related potential problem arising with rotational movement generated by exerting torque on a proximal end of a long probe is "chatter", wherein force stored in the probe's twist suddenly overcomes friction and jumps forward (uncontrolled release of torsion). This may affect dosing (e.g., by "skipping" some areas, while potentially over-dosing others). In some embodiments, dose delivery is adjusted to compensate for such changes; e.g., by speeding up motion and/or reducing plasma generation while the probe is "stuck", and/or by scheduling a return to areas which were "jumped over" in order to dose them more slowly. Optionally, command/movement mismatch is partially compensated for in an anticipatory fashion, by reducing plasma delivery when the probe is under high enough strain and/or stress that a sudden release (with concomitant loss of dosage control) may be imminent. Plasma generation may then resume during a post-release period when motion velocity is better controlled.

Rotational offsets due to twisting can be measured via strain sensors along the probe (e.g., a fiber optic strain sensor), or the rotational position of the plasma generating module can be measured directly, e.g., using magnetic field sensing, fluoroscopic observation of a radiopaque marker, or another method.

The principle applies more generally that when precise robotic control of a plasma generating module is partially lacking (for example, because the probe itself is long and/or thin, and subject to twisting and/or bending motions), dosing rate control can be used to compensate for under- and/or over-exposures which might otherwise occur. For example, a plasma delivery probe may build up a mismatch between actual position and a position expected from commanded movements because of resistance forces (e.g., friction) in its environment. Additionally or alternatively, it may deviate from commanded movements due to releases of resistance forces (e.g., release of friction and/or overcoming a barrier, for example, overcoming the barrier by penetrating and/or sliding off of it).

Figure 7A:
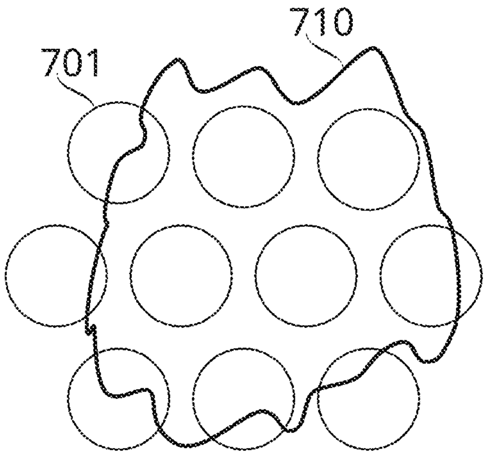
FIG. 7A-7B schematically represent static-dwell patterns of plasma delivery across a surface area, according to some embodiments of the present disclosure.
Figure 7B:
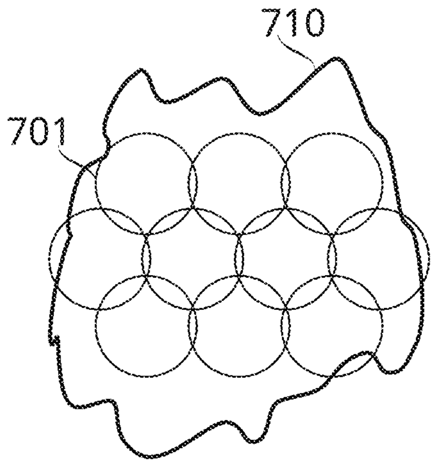

Reference is now made to FIG. 7A-7B, which schematically represent static-dwell patterns of plasma delivery across a surface area 710, according to some embodiments of the present disclosure.

In both FIGS. 7A, and 7B, the circles 701 represent roughly the area over which a plasma plume directly plays during a single period of static dwell (e.g., a period of about 5-360 seconds). In FIG. 7A, although the pattern leaves areas which do not directly receive plasma contact, treatment effects may still extend continuously throughout the area of coverage, e.g., due to diffusion of reactive species. In FIG. 7B, plasma contact areas have been brought closer together, potentially improving evenness of the distribution of treatment effects. The pattern in which different static dwell locations are treated can put them in any order. For example, the sites may be scanned in a sequential rastering (e.g., left to right, and top to bottom), in a random order, or in an order that avoids treating adjacent areas immediate after one another.

While referred to above as locations of "static dwell", circles 701 may alternatively delineate areas within which some confined pattern of plasma plume motion occurs. For example, the center of the plasma plume may be swept in a circle, optionally for a plurality of cycles during any individual "dwell". This potentially helps to even out hot spots/dead zones by use of temporal averaging.

Figure 8:
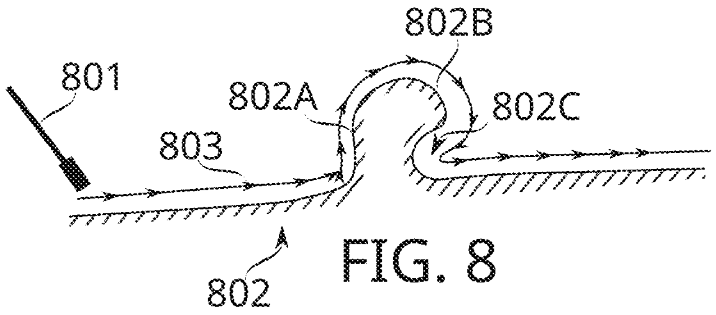
FIG. 8 schematically represents control of the motion of a plasma generating probe over a protruding structure, according to some embodiments of the present disclosure.

Reference is now made to FIG. 8, which schematically represents control of the motion of a plasma generating probe 801 over a protruding structure 802, according to some embodiments of the present disclosure. In the example, plasma probe 801 travels along the line of motion indicated by the arrows 803. In some embodiments, the motion is pre-planned, e.g., to follow a 3-D structure previously determined by imaging.

Additionally or alternatively, in some embodiments, the probe is maintained at an appropriately selected distance from the tissue, with the distance being monitored, e.g., by monitoring the efficacy of power delivery into the plasma plume, by use of a proximity sensor, and/or or by direct imaging of its position.

As the probe nears the rise of tissue near region 802A, changes in sensing may indicate that the probe is "too close" to its target. The sensing can take one or more of several forms. For example, there may be resistance to moving (if the probe is actually low enough to contact the protrusion), the probe may be found to be positioned out of the zone where plasma impedance is sensitive to distance changes, there may be an impediment to the flow of ionization gas, a proximity sensor may provide an indication of a change in distance—or the probe/tissue distance may be tracked by an imaging method such as X-ray or ultrasound imaging.

After position adjustment, Lateral translation resumes, until a distance measurement again goes out of its targeted range at region 802B. For example, the plasma plume may weaken as a result of a decrease in target-coupled impedance. In reaction, automatic control of the probe may bring the probe closer to the target until the detected distance (e.g., detected via plume impedance or another sensor such as a proximity sensor) is restored to a targeted magnitude. While the example of a protruding is described, the surfaces of indented areas (e.g., as may occur following a resection) may also be followed by use of tracking.

The overhang region at 802C, in some embodiments, may be known in advance from imaging, or local sensing may be sufficiently sensitive to detect it. However, when such overhang regions are known to be a common feature in treatment areas (e.g., if protruding structure 802 is a polyp), it may simply be assumed that such an overhang may exist, and probe motions planned accordingly.

One way to handle the overhang is—while or after lowering the probe slightly—also moving the probe laterally a small amount back in the direction it came from. This potentially helps push away part of protruding structure 802, revealing more of region 802C. On the leading edge (at 802A), the protruding structure may similarly be pushed out of the way in order to help expose areas partially sheltered by the protruding structure itself.

It is noted, furthermore, that in the course of scanning the plasma delivery probe over protruding structure 802, data indicative of movements and distance sensing by the probe are optionally used to generate a 3-D map of the protruding structure 802 itself. For example, places where probe height was adjusted to maintain a targeted power level correspond to 3-D features of the surface. A map may be used as a basis for the planning of further movements. For example, a plasma delivery probe may be scanned around the perimeter, and optionally angled to point "under" the protruding structure to help ensure coverage of potentially sheltered areas.

Use of Dosimetry for Distance Control

Figure 9A:
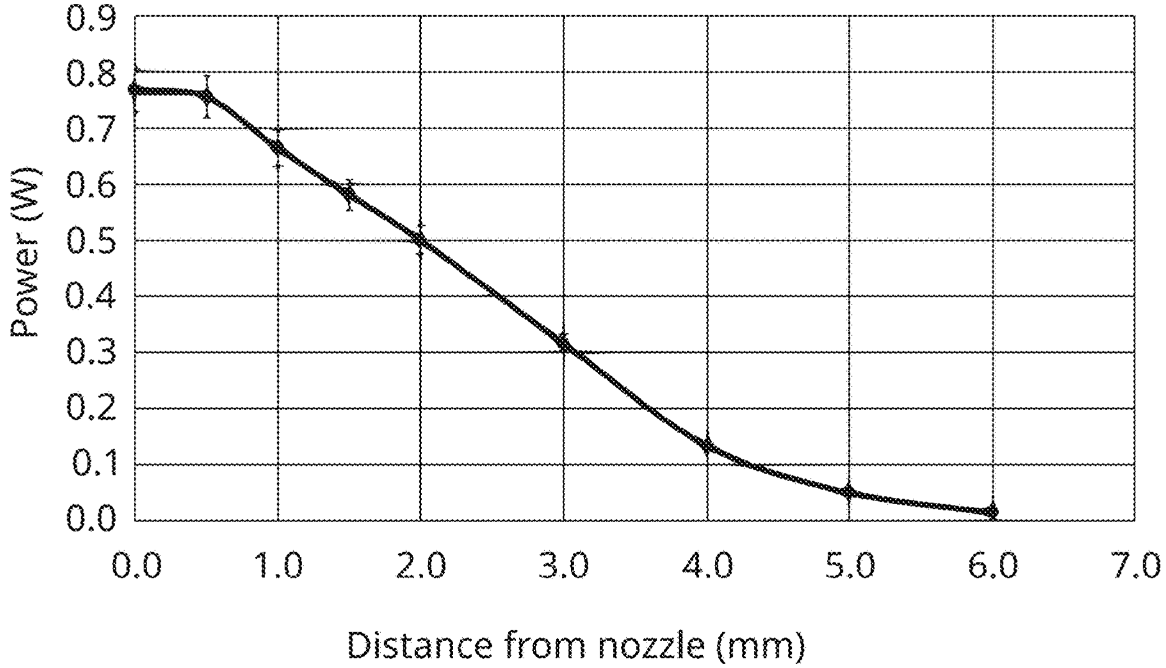
FIG. 9A graphs relative power output from a plasma plume as a function of distance from a nozzle (exit aperture of a plasma delivery probe), according to some embodiments of the present disclosure.

Reference is now made to FIG. 9A, which graphs relative power output from a plasma plume as a function of distance from a nozzle (exit aperture of a plasma delivery probe), according to some embodiments of the present disclosure.

Probe tip distance, in some embodiments of the present disclosure, has a direct and characterizable influence on the measured dosage of plasma delivery to tissue. Conversely, other things being equal, measurements of plasma dosage can indicate the proximity of the plasma probe tip to a surrounding tissue.

FIG. 9A demonstrates a result from an experiment that ties non-thermal atmospheric plasma (NTAP) output (measured in terms of electrical power consumed by plasma generation) to distance from target. It may be seen from the chart that power consumption as a measure of plasma dosage may be used as an indirect measurement of distance to the target tissue, e.g., at 500 mW of power, the distance of the target from the nozzle is about 2 mm.

Uses of such a curve, in some embodiments of the disclosure, optionally include using a dosimetry measure (e.g., power output) for one or more of:

1. A proxy for probe proximity to target.
2. Evaluating probe actual position (measured by another method) against position estimated from the dosimetry measure. This is used, for example, to verify that plasma generation is within expected parameters—e.g., there is no unexpected attenuation of plasma generation due to probe damage and/or contamination. In some embodiments, deviation between an actual and an expected dosimetry measurement value is related to the generation of secondary plasma effects, for example as described in the next section. Examples of other methods of measuring probe position include measurements using position sensing, distance sensing, and/or contact, for example as described in relation to sensor 32A.
3. Position control to create a virtual spacer (i.e., maintain a defined distance from the target). For example, the position of a probe is advanced or withdrawn in a longitudinal direction as it scans laterally (i.e., roughly perpendicular to the longitudinal direction) over a target to maintain an approximately constant dosimetry measurement value.
4. More generally, as feedback for controlling distance to tissue whether constant or not; for example to maintain a larger distance while scanning a more irregular and/or unpredictable (e.g., moving) surface, or a closer distance while scanning a more regular and/or more predictably positioned surface. Optionally, speed of scanning is adjusted concomitant with changes in delivered dose per unit time in order to maintain an overall targeted plasma dosing level.
5. Mapping 3-D structure of a surface, in cooperation with a positioning system (e.g., a robotic positioning system). For example, together with knowledge of the movements of a tip of the plasma delivery nozzle in space, the dosimetry measure gives an indication of the distance of the surface being treated beyond the tip of the plasma probe. The plasma delivery nozzle may move in a plane or known smooth curve, for example (e.g., a portion of a spherical or ellipsoidal surface). The variable distances of the treated surface from the nozzle position can be added to this surface of movement to determine a surface map.

Use of Dosimetry for Plasma Plume Orientation Control

In some embodiments, a plasma jet is intended to be aimed in a certain direction. Gas ionization (ignition) may nevertheless occur in locations outside the plasma jet. This may occur, for example, next to the dielectric barrier alongside the electrode in the presence of residual ionization gas. As a result, secondary (parasitic) plasma may route towards the proximal (back) side of the tip. Additionally or alternatively, a secondary plasma effect may arise when sufficient target capacitance is generated to attract plasma. Gas media either trapped or stagnated around the probe tip is ionized, thus creating a secondary plasma and ionization of the trapped/stagnated gas. This effect may result in higher concentration of gas ionization.

Plasma outside the jet is used, in some embodiments, as a feature with deliberate applications. Additionally or alternatively, in some embodiments, control is exercised to limit such plasma generation, e.g, in order to mitigate heating effects.

For example, knowing the current power output of the probe, and also knowing its distance from a target, a calibration curve such as that of FIG. 9A may reveal that more power is being dissipated than expected. This is interpreted, in some embodiments, as an indication that secondary plasma effects are occurring.

In some embodiments, positioning of the plasma delivery probe is adjusted in response to this indication—for example, to increase or decrease secondary plasma effects. Adjustment may include, for example, altering an orientation of the plasma probe so that plasma and/or ionization gas are routed to flow along different pathways. This in turn may extend or minimize the heating of slow moving, trapped, or stagnated gas.

Additionally or alternatively to a power dosimetry measurement, temperature measurement may be used as an indication of plasma generation (e.g., disturbance from an expected value due to secondary plasma effects). A temperature or other sensor may be located at a particular location relative to a probe to provide particular sensitivity to secondary plasma effects, for example, outside the probe and longitudinally alongside a discharge electrode (e.g., on a probe outer surface). In some examples, the sensor comprises one or more electrodes, positioned to sense voltages established in the vicinity of the probe which may contribute to and/or be affected by secondary plasma effects.

In some embodiments, probe orientation is adjusted automatically, based on sensor feedback, a model that accounts for the sensor feedback, and/or modeling of how much secondary plasma routing a particular configuration is likely to generate. For example, a probe may be re-oriented within a lumen so that a pattern of gas flow generated from it does not lead to stagnation in the vicinity of the probe itself (e.g., stagnation at a location behind an aperture from which the plasma plume exits). Such adjustments may be performed generally in conjunction with flow-controlled dosing, for example as described in relation to FIGS. 5A-5B, herein. Additionally or alternatively, receiving an indication that secondary plasma effects are occurring may be a trigger for accelerating movement of the plasma delivery probe and/or reducing power delivery.

Measurement of Reactive Species

Figure 9B:
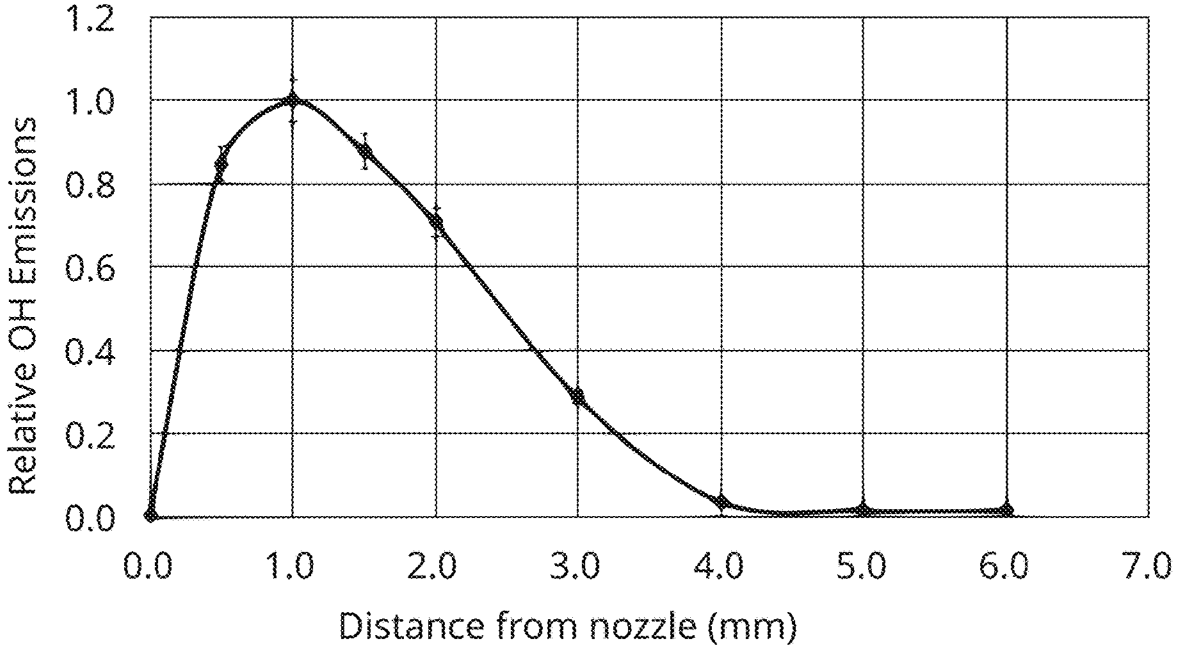
FIG. 9B graphs relative hydroxyl (OH·) emissions from a plasma plume as a function of distance from nozzle, according to some embodiments of the present disclosure.
Figure 9C:
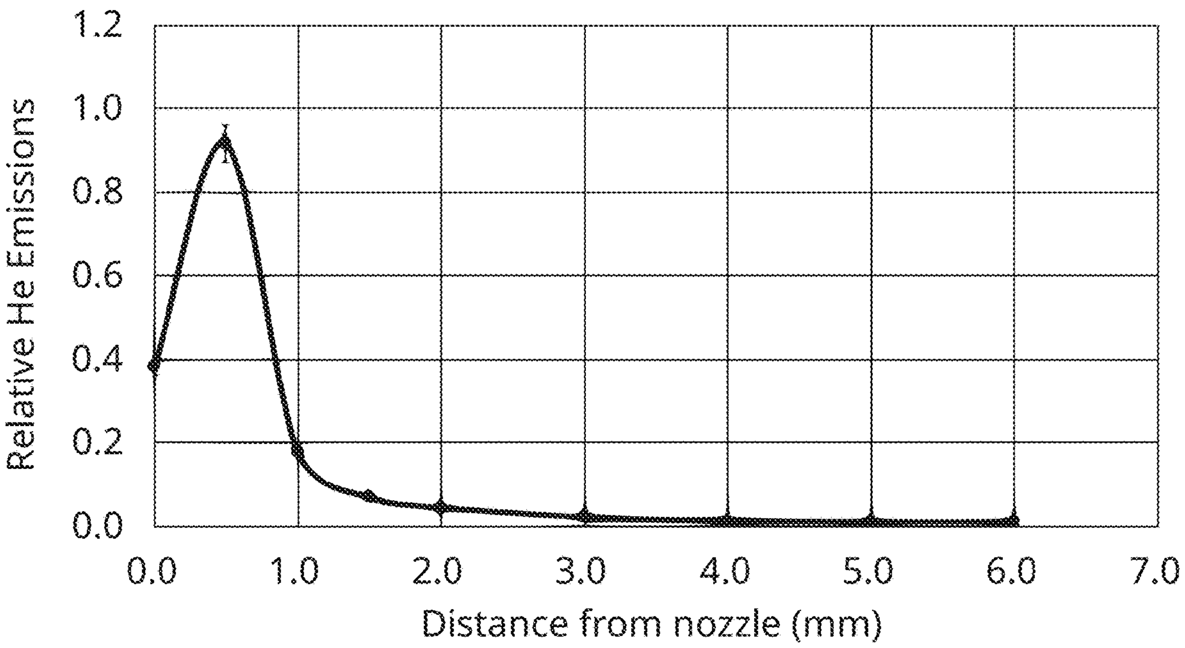
FIG. 9C graphs relative helium (He) emissions from a plasma plume as a function of distance from nozzle, according to some embodiments of the present disclosure.

Reference is now made to FIG. 9B, which graphs relative hydroxyl (OH) emissions from a plasma plume as a function of distance from nozzle, according to some embodiments of the present disclosure. The monitoring wavelength is 308.9 nm. Reference is also made to FIG. 9C, which graphs relative helium (He) emissions from a plasma plume as a function of distance from nozzle, according to some embodiments of the present disclosure. The monitoring wavelength is 706 nm.

Measurement of reactive species (for example, via measurement of the amplitude of one or more spectral emission peaks associated with particular species) within generated plasma provides feedback on the amount of effective plasma that is generated through ionizing gas within a given environment.

In some embodiments, in-situ measurement of reactive species is performed using cleaved collimated fibers (e.g., integrated into the plasma probe) connected to a spectroscopy measurement device. This provides an option for real-time measurement that directly monitors constituents of plasma.

As described, for example, herein in relation to FIGS. 1B and/or 2A-2D, real-time measurement can provide feedback on the potency of the generated plasma as it reacts with the surrounding environment. It can also provide feedback on the depletion of surrounding elements in the environment which may result in reduction of plasma potency (e.g., drying of the environment may reduce production of OH reactive species). The graphs of FIGS. 9B-9C show spectroscopy measurements as a function of target distance from a nozzle. The graphs overall may themselves vary as a function of power.

In some embodiments, such spectral measurements are integrated over time to indicate the potency of the plasma treatment, e.g., per area and/or overall.

In some embodiments, such spectral measurements are used to estimate and optionally control plasma delivery and/or plasma effects. Control optionally comprises changing, for example, one or more of the group consisting of: a spatial pattern of probe movement, a rate of probe movement, a level of electrical power delivery, a rate of ionization gas delivery, a composition of delivered ionization gas, and/or control of conditions at the site (e.g., wetting the site to enhance secondary generation of OH reactive species). In some embodiments, more particularly, adjustment of the composition of delivered ionization gas and/or conditions at the site is responsive to measured levels of reactive species, e.g., the adjustment is selected to target particular level(s) of one or more reactive species.

In some embodiments, the spectral characteristics of the environment and the current state of ionization gas in the cavity/volume (materials already at the site of the treatment) can be used to anticipate the resulting production of reactive species (e.g., oxygen and nitrogen species) at different levels of plasma ionization (e.g., as measured by an indicator such as a helium emission peak). In some embodiments, an appropriate ionization level and/or gas composition is provided according to the estimate and/or measurement of reactive species production.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have 25 specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

It is the intent of the applicant(s) that all publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting. In addition, any priority document(s) of this application is/are hereby incorporated herein by reference in its/their entirety.

What is claimed is:

1. A system for providing a controlled plasma dosage to a target region of tissue of a subject, the system comprising:

a plasma delivery probe;

a motion controller configured to move a plasma plume produced from the plasma delivery probe; and a processor and a memory storing processor instructions which instruct the processor to:

access a specification of a total specific dosage specifying a targeted range of effective plasma dose per unit of tissue to be delivered by the plasma delivery probe to sub-regions of the target region of the tissue, calculate a plan for operation of the plasma delivery probe, including rate of plasma delivery and movements to deliver the total specific dosage to the target region, and instruct the motion controller to move the plasma plume according to the movements while the plasma delivery probe operates to provide plasma;

wherein, for each of at least one of the sub-regions:

the movements together with the rate of plasma delivery are calculated to deliver a delivered total specific dosage to the sub-region corresponding to the specified target range of effective plasma dose per unit tissue, and the delivered total specific dosage of the sub-region includes delivery to the whole sub-region from each of a plurality of positions of the plasma plume during the movements; and for each of said at least one of the sub-regions, the processor instructions further instruct the processor to:

receive an indication of a rate of actual plasma delivery to the sub-region, determine that the indicated rate, together with the movements to position the plasma plume at the plurality of positions, may not produce the specified total specific dosage of plasma for the sub-region, adjust the plan for operation of the plasma delivery probe so that actually delivered total specific dosage of plasma in the sub-region satisfies the specification of the total specific dosage of effective plasma, and operate the plasma delivery probe according to the adjusted plan, while still providing the specified total specific dosage to the rest of the target region.

2. The system of claim 1, wherein the processor adjusts the plan for operation of the plasma delivery probe by a modification to the movements based on said determination that the specified total specific dosage may not be produced.

3. The system of claim 2, wherein the modification to the movements comprises changing a speed of movement of the plasma delivery probe.

4. The system of claim 2, wherein the modification to the movements comprises changing a position of the plasma delivery probe.

5. The system of claim 1, comprising at least one sensor configured to measure the rate of plasma delivery, and wherein the processor receives the indication of the rate of actual plasma delivery from the at least one sensor.

6. The system of claim 5, wherein the at least one sensor measures power dissipated by plasma generation.

7. The system of claim 5, wherein the at least one sensor comprises a temperature sensor.

8. The system of claim 5, wherein the at least one sensor comprises a spectral emission detector configured to measure spectral emissions from the plasma.

9. The system of claim 5, wherein the at least one sensor comprises a position sensor configured to measure a current position of the plasma delivery probe.

10. The system of claim 5, wherein the at least one sensor is positioned near a distal end of the plasma delivery probe.

11. The system of claim 1, wherein the movements include a plurality of locations within the target region at which movement of the plasma delivery probe pauses while the plasma delivery probe delivers plasma.

12. The system of claim 11, wherein the indication of the rate of actual plasma delivery comprises a measurement of a flow of ionization gas to the plasma plume; and the operation of the plasma delivery probe is adjusted by slowing movement of the plasma delivery probe in response to a decrease in the flow.

13. The system of claim 11, wherein the indication of the rate of actual plasma delivery comprises a measurement of a flow of ionization gas to the plasma plume; and the operation of the plasma delivery probe is adjusted by withdrawing the plasma delivery probe in response to a decrease in the flow.

14. The system of claim 1, comprising a rigid introducer having a lumen sized to introduce the plasma delivery probe through the lumen to the target tissue region, internal to the subject.

15. The system of claim 14, wherein the movements include at least one of inserting and withdrawing the introducer while plasma is delivered continuously from the plasma delivery probe.

16. The system of claim 1, wherein the movements comprise a contiguous pathway along which the plasma delivery probe continuously moves while delivering the plasma.

17. The system of claim 16, wherein the delivery of the plasma is onto successive contiguous surface regions along the contiguous pathway.

18. The system of claim 1, wherein the indication is a measured reduction in the power dissipated by plasma generation, and the operation of the plasma probe is adjusted by moving the plasma delivery probe towards the target region.

19. The system of claim 18, wherein the processor selects a distance of the movement towards the target region according to the magnitude of an increase in measured power as the plasma probe is moved toward the target region.

20. The system of claim 19, wherein the processor halts movement of the probe towards the target region upon the measured power reaching a substantially constant level.

21. The system of claim 1, wherein the indication of the rate of actual plasma delivery is an indication of a spatial pattern of gaseous flow near the target region of tissue; and operation of the plasma delivery probe is adjusted to modify said spatial pattern of gaseous flow.

22. The system of claim 1, wherein the effective dose unit is defined as plasma dose per area and/or volume.

23. The system of claim 1, wherein said processor instructions of determining comprise calculating the actual dosing based on modeled considerations comprising one or more of: dynamics of plasma flow, plume temperature, diffusion constants of reactive species in tissue, and/or time constants of reactive species decay.

24. The system of claim 1, wherein said processor instructions further comprise:

receiving an indication of a distance of the plasma delivery probe from tissue in the sub-region, and determining that the indicated rate and distance together with the movements to position the plasma plume at the plurality of positions, may not produce the specified total specific dosage of plasma for the sub-region.

25. The system of claim 1, wherein said processor instructions further comprise:

calculating an additional one or more movements and one or more corresponding rates of plasma delivery based on the determination, such that delivery of plasma during the additional movements compensates for the determined insufficiency in actual dosage delivered to the sub-region, and adjusting the plan for operation of the plasma delivery probe by including the calculated additional movements and corresponding rates of plasma delivery.

26. The system of claim 1, wherein the processor instructions further comprise:

stopping or attenuating plasma delivery upon an indication that an estimated effective plasma delivery has reached the specified total specific dosage of plasma for the sub-region, and directing the motion controller toward a different sub-region of the target.

27. The system of claim 1, wherein the processor instructions comprise calculating an initial plan for operation of the plasma delivery probe prior to delivery of plasma to the target region, and adjusting the initial plan based on the determination that the specified total specific dosage may not be produced.

28. A system for providing a controlled plasma dosage to a target region of tissue of a subject, the system comprising:

a plasma delivery probe;

a motion controller configured to move a plasma plume produced from the plasma delivery probe; and a processor and a memory storing processor instructions which instruct the processor to:

access a specification of a total specific dosage specifying a targeted range of effective plasma dose per unit of tissue to be delivered by the plasma delivery probe to sub-regions of the target region of the tissue, and detect movements of the plasma plume;

for each of at least one of the sub-regions:

the delivered total specific dosage of the sub-region includes delivery to the whole sub-region from each of a plurality of positions of the plasma plume during the movements; and for each of said at least one of the sub-regions, the processor instructions further instruct the processor to:

receive an indication of a rate of actual plasma delivery to the sub-region, determine that the indicated rate of actual plasma delivery, together with the detected movements, may not produce the specified total specific dosage of plasma for the sub-region, adjust operation of the plasma delivery probe so that actually delivered total specific dosage of plasma in the sub-region satisfies the specification of the total specific dosage of effective plasma, wherein the adjusted operation modifies one or both of movement of the probe and plasma delivery from the probe, while still providing the specified total specific dosage to the rest of the target region.

* * * * *